(12) United States Patent
Kopacka et al.

(10) Patent No.: US 9,939,379 B2
(45) Date of Patent: Apr. 10, 2018

(54) COMPACT ANALYZER FOR ACQUIRING CHARACTERISTICS OF SMALL TABS PLACED IN A VESSEL

(71) Applicant: PharmaSeq, Inc., Monmouth Junction, NJ (US)

(72) Inventors: Wesley Kopacka, Kingston, NJ (US); Wlodek Mandecki, Princeton Junction, NJ (US); Richard Morris, Ringoes, NJ (US)

( * ) Notice: Subject to any disclaimer, the term of this patent is extended or adjusted under 35 U.S.C. 154(b) by 600 days.

(21) Appl. No.: 14/053,938

(22) Filed: Oct. 15, 2013

(65) Prior Publication Data

US 2014/0106470 A1     Apr. 17, 2014

Related U.S. Application Data

(60) Provisional application No. 61/713,825, filed on Oct. 15, 2012.

(51) Int. Cl.
*G01N 21/64* (2006.01)

(52) U.S. Cl.
CPC ....... *G01N 21/6428* (2013.01); *G01N 21/645* (2013.01)

(58) Field of Classification Search
None
See application file for complete search history.

(56) References Cited

U.S. PATENT DOCUMENTS

| | | | | |
|---|---|---|---|---|
| 2001/0044109 A1* | 11/2001 | Mandecki | ..... | 435/6 |
| 2002/0006673 A1* | 1/2002 | Mandecki | ..... | 436/518 |
| 2004/0029109 A1* | 2/2004 | Lai | ..... | 435/5 |
| 2006/0023219 A1* | 2/2006 | Meyer et al. | ..... | 356/432 |
| 2006/0256338 A1* | 11/2006 | Gratton et al. | ..... | 356/417 |
| 2007/0021929 A1* | 1/2007 | Lemmo et al. | ..... | 702/22 |
| 2010/0322494 A1* | 12/2010 | Fauver et al. | ..... | 382/131 |
| 2015/0086971 A1* | 3/2015 | Botma | ..... | G01N 35/10 435/3 |

OTHER PUBLICATIONS

Braeckmans, K, DeSmedt, SC, Leblans, M, Pauwels, R, Demeester, J. "Encoding microcarriers: present and future technologies". Nature Reviews Drug Discovery; (1); p. 447-456; (2002).*
Mandecki, W, Barbara, A, Coradetti, T, Davidowitz, H, Flint, JA, Huang, Z, Kopacka, WM, Lin, X, Wang, Z, Darzynkiewicz, Z. "Microstransponders, the miniature RFID electronic chips, as platforms for cell growth in cytotoxicity assays" Cytometry Part A; (69A); p. 1097-1105; (2006).*

* cited by examiner

*Primary Examiner* — Jill A Warden
*Assistant Examiner* — Benjamin R Whatley

(57) ABSTRACT

Provided among other things is an analyzer for use with tabs placed in a vessel including: a stochastic sampling device adapted to receive the vessel; a light beam source adapted to enter the moving vessel and selectively illuminate tabs; an analytical signal receiver adapted to receive a signal indicative of an analytical process occurring on the surface of the tab as the tab is selectively illuminated; a tab ID receiver adapted to collect ID data from the tabs in coordination with their selective illumination; and a controller for associating identified tabs with analytical signals.

1 Claim, 15 Drawing Sheets

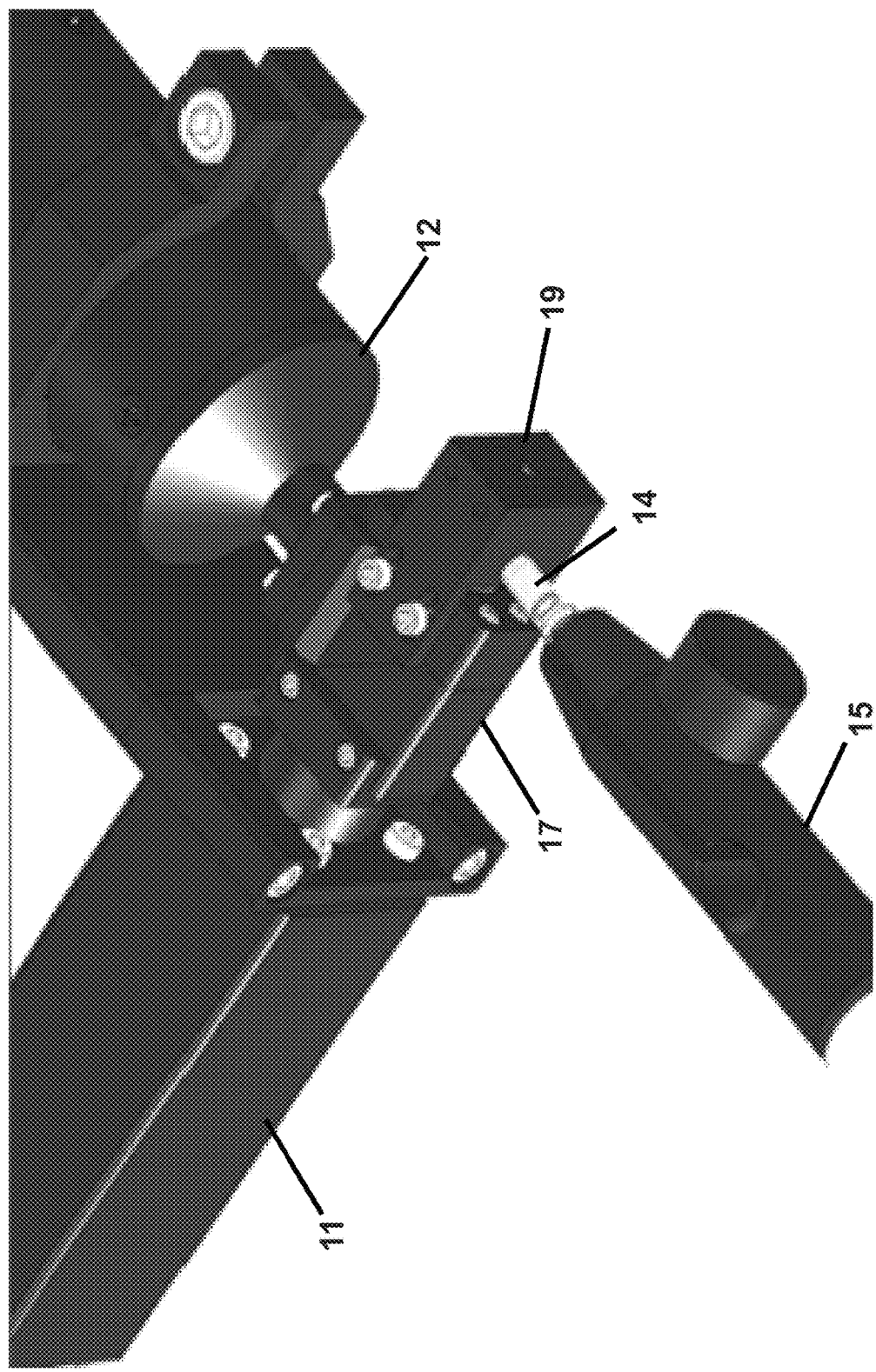

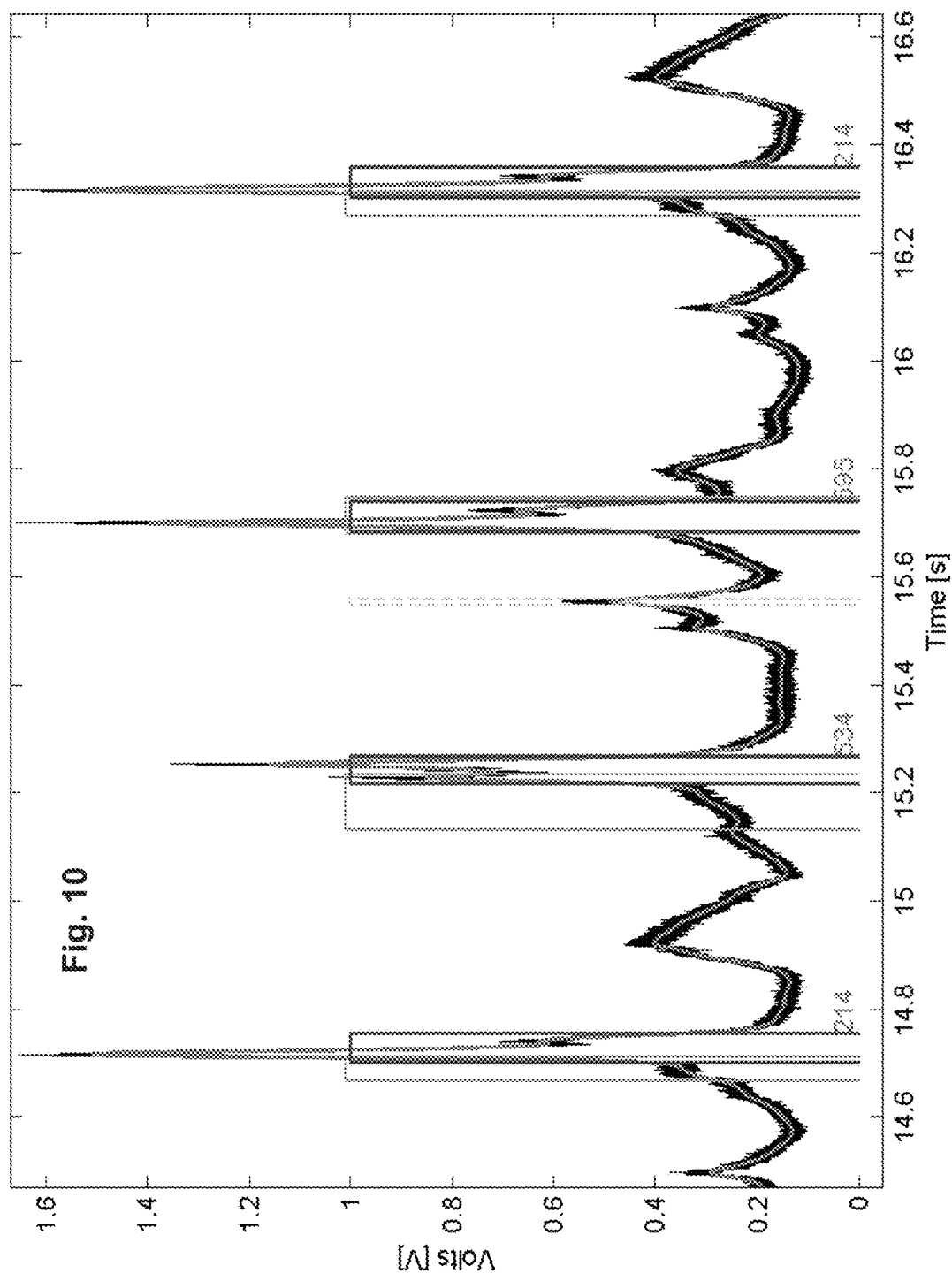

COMPACT ANALYZER FOR ACQUIRING CHARACTERISTICS OF SMALL TABS PLACED IN A VESSEL

CROSS-REFERENCE TO RELATED APPLICATIONS

This application claims benefit of U.S. Provisional Patent Application 61/713,825 entitled "COMPACT ANALYZER FOR ACQUIRING CHARACTERISTICS OF SMALL TABS PLACED IN A VESSEL", filed Oct. 15, 2012, herein incorporated in its entirety by reference.

Provided is an efficient device and method for reading multiple tabs adapted for conducting a surface analytical chemistry, such as beads, chips, or the like.

The current invention works with small objects ("tabs", e.g., beads, chips, and the like) that have an analytical surface adapted to yield a light responsive analytical signal, such as light absorption or emission. The tabs have an associated identifier (ID), such as 1-dimensional or 2-dimensional bar code, where the association is such that if a focused light beam triggers the identifier, it will also provide for the light responsive analytical signal.

The current invention has been initially tested with very small, light-triggered microtransponders ("MTPs" or "p-Chip" microtransponders), such as described in U.S. Pat. No. 7,098,394. These are available to provide identifiers, for example as identifiers used in conjunction in nucleic acid assays (e.g., assays using DNA, RNA, or analogs thereof). These have proven to be stable under a variety of conditions. However, the invention can function with other tabs.

Currently, flow cytometry methods, such as found in the FlexMAX 3D™ instrument (Luminex Corporation, Austin, Tex.), provide multiplexing options for bead-based assay systems. These are reliant on great complexity, and do not provide the option for multiplexed time-dependent data.

Provided herein is a simple system that relies on the statistical sampling of chips that are aligned with the detection apparatus periodically while being mixed in a small volume.

SUMMARY

Provided among other things is an analyzer for use with tabs placed in a vessel comprising: a stochastic sampling device adapted to receive the vessel; a light beam source, the light adapted to enter the moving vessel and selectively illuminate tabs; an analytical signal receiver adapted to receive a signal indicative of an analytical process occurring on the surface of the tab as the tab is selectively illuminated; a tab ID receiver adapted to collect ID data from the tabs in coordination with their selective illumination; and a controller for associating identified tabs with analytical signals. In one embodiment, the stochastic sampling device is adapted to mix the contents of the vessel such that 80% of the tabs are sampled within an analytically useful time period. The stochastic sampling device can for example rotate the vessel, be adapted to rail tabs against a side of the vessel closest to the light beam source, translate the vessels back and forth, and the like. The analyzer can comprise the vessel, which vessel can be closed.

In certain embodiments, the analytical signal receiver is a light sensor, such as a fluorescence sensor. In certain embodiments the tab ID receiver is a microtransponder ID radio receiver adapted to collect ID data from the tabs that are light-responsive microtransponders as they are selectively illuminated.

In certain embodiments, the analyzer is adapted to hold 10 to 100 tabs, and the mixing device is adapted to rotate the vessel such that 80% of the tabs are sampled within 100 seconds, to hold 10 to 10,000 tabs, and the mixing device is adapted to rotate the vessel such that 80% of the tabs are sampled within 1000 seconds.

In certain embodiments, the analytical signal receiver and the ID receiver share detection elements, but the controller parses analytical signal and ID signal from the data stream. For example, the ID receiver and/or the analytical signal receiver are a spatially-resolved receivers (such as a CCD), or a shared spatially-resolved receiver.

The invention provides a kit comprising an analyzer, and one or more of (a) the vessel adapted for use in the analyzer or (b) tabs adapted for use with the analyzer, such as light-triggered microtransponders.

Provided is a method of analyzing tabs, comprising: stochastically sampling tabs in a vessel; directing light at the vessel; sufficiently intersecting the collimated light with an analytical surface on a said tab so as to allow association of an analytical signal from the analytical surface with the illumination; determining an ID associated with the tab aligned with the tab as the analytical signal is generated; reading the analytical signal and associating the identifier and the signal; and continuing the stochastic sampling until 80% of the tabs are so sampled. The method can comprise conducting the method over time and repeatedly reading tabs such that time-response data is collected.

Further provided is a light-triggered microtransponder reader for light-responsive microtransponders placed in a vessel comprising: a stochastic sampling device adapted to receive the vessel; a source of light adapted to enter the moving vessel and selectively illuminate microtransponders; and a microtransponder ID radio receiver adapted to collect ID data from the microtransponders as they are selectively illuminated. Another embodiment of the reader operates with tabs and a tab ID receiver. The analyzer is a species of the reader.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only illustrative embodiments of this invention and are therefore not to be considered limiting of its scope, for the invention may admit to other equally effective embodiments.

FIG. 9A illustrates another prototype of the analyzer.

FIG. 10 provides modeled readout of three fluorescently labeled MTPs on the analyzer. Noisy lines—raw PMT data, Line within noisy lines—denoised PMT data, Light-lined bar shape—bounds of decode data, Dark-lined bar shape—synced adjustment of decode to PMT peak with decode ID at lower right (each dark-lined pillar), dotted—peak with no ID read. As part of preliminary modeling, the chips were glued to the wall of the vial (separation of 120°).

Figure 1:
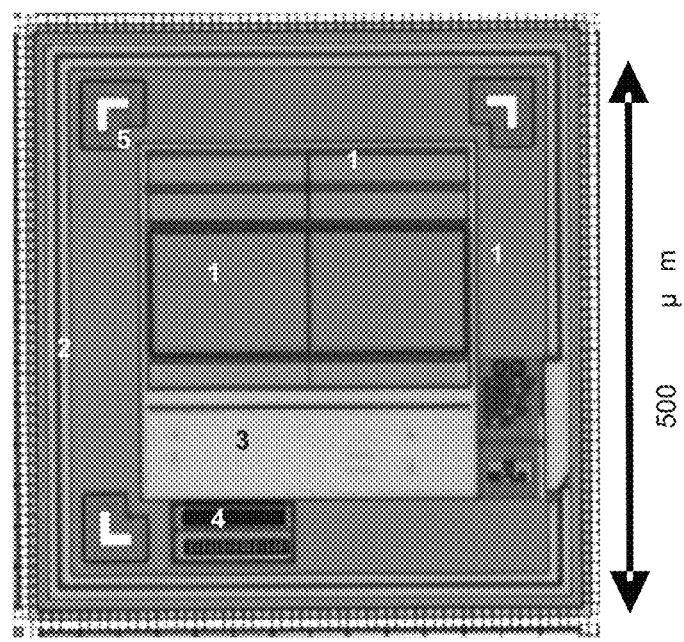
FIG. 1 shows a 30-bit MTP. Key elements are: 1) photocells; 2) antenna; 3) logic; 4) memory; 5) registration marks.

To facilitate understanding, identical reference numerals have been used, where possible, to designate comparable elements that are common to the figures. The figures are not drawn to scale and may be simplified for clarity. It is contemplated that elements and features of one embodiment may be beneficially incorporated in other embodiments without further recitation.

DETAILED DESCRIPTION

Figure 8:
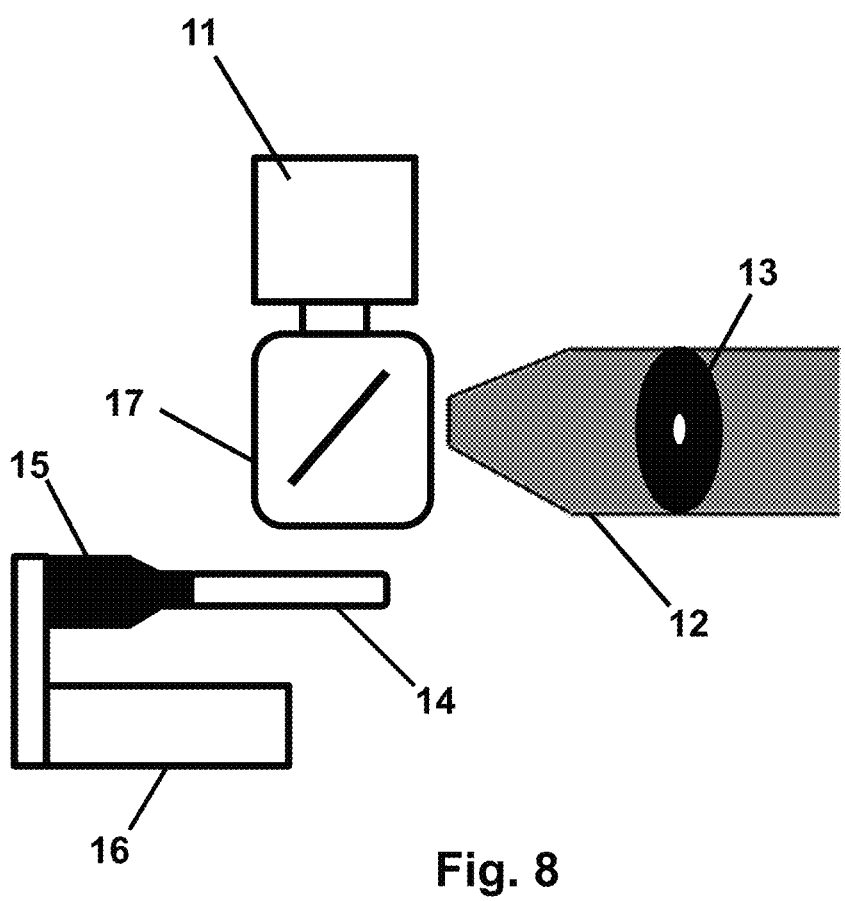
FIG. 8 illustrates a prototype of the analyzer. 11: photomultiplier tube (PMT); 12: wand; 13: amplifier board; 14: sample vessel (tube); 15: holder being moved and rotated with stepper motor; 16: housing of stepper motor assembly; 17: filter cube.

An exemplary embodiment is shown in FIG. 8. It includes a cut-away of a portion of the illustrated wand 12. The holder 15 is rotated and optionally moved along the primary axis of the sample vessel 14 by one or more motors, such as stepper motors. The filter cube can contain for a mirror by which the laser from wand 12 is directed towards vessel 14, and which is adapted to pass (without reflection) the wavelength of any induced fluorescence to the PMT 11.

Figure 9B:
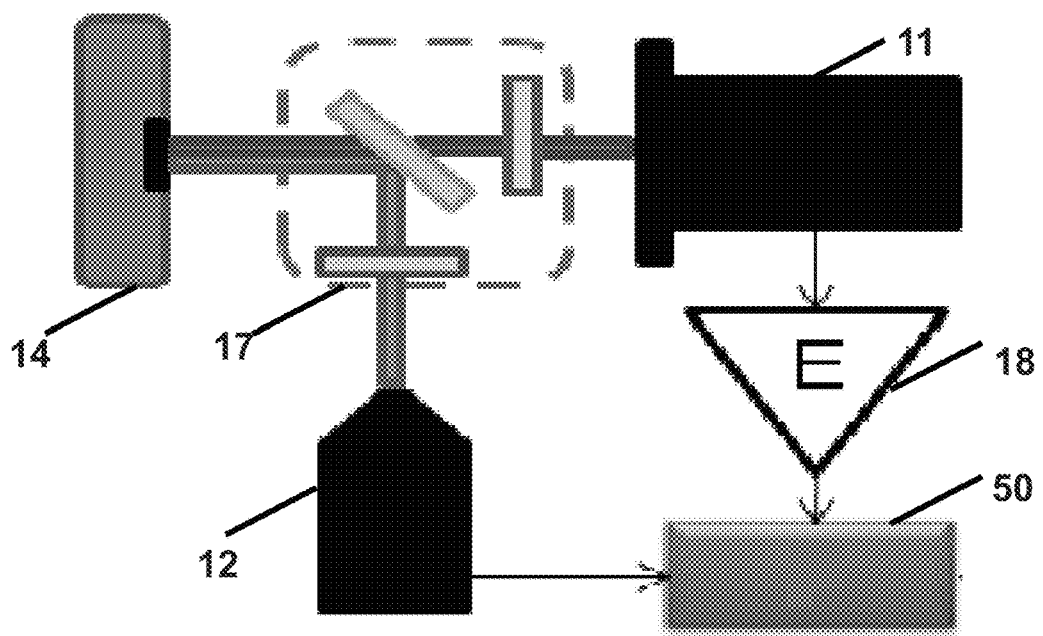
FIG. 9B illustrates a conceptual schematic of the analyzer.

FIG. 9 shows another exemplary embodiment. The mechanical assembly includes two stepper motors to provide two degrees of freedom, translation and rotation, for the sample vial (e.g., Roche's 100 microliter capillary). The vial can contain for example MTPs in a solution void of any air gaps.

The optical assembly is designed to activate the ID circuitry of MTPs as well as to excite the fluorophore conjugated to the MTPs surfaces. The fluorescent channel is optimized for example for Cy5.5 and Alexa Fluor 660 fluorophores, and consisted of a 660 nm single-mode laser diode (e.g., Opnext HL6545MG) focused by a lens (e.g., Thorlabs A230TM-B aspheric lens, f=4.51 mm, NA=0.54). A custom filter cube 17 contains Ø6 mm emission and excitation filters (Semrock FF01-661/11 and FF01-692/LP, respectively) and a dichroic beam splitter (e.g., 7×10 mm Semrock FF677-Di01 dichroic beam splitter). The RF pickup coil is for example located at the filter cube output window, and a pinhole assembly 19 is mated the vial to the window for better control of the illumination area. A photomultiplier tube 11 (e.g., Hamamatsu H5784-20) couples to the filter cube, with an overall path length of 35 mm from the vial, to measure fluorescence.

Linear and rotational movements of the vial are controlled for example via an Arcus Technology PMX-4CX-SA motor controller. A commercial PharmaSeq ID reader [7], for example, decodes MTP IDs at the same time that the PMT collects their fluorescence. Data streams from the ID reader and PMT are processed using a data acquisition device ("DAQ", e.g., Measurement Computing USB-1608FS), with the PMT data stream first passing through a denoising analog low-pass filter. All control and data acquisition interfaces with a computer via USB.

The two stepper motors needed to manipulate the vial can be, for example, controlled using Arcus Technology's standard graphical user interface (GUI). Another GUI can for example control the ID reader and interface with the DAQ. The data streams can be sampled for example at 20 kHz per channel with 16-bit resolution. After parsing, the DAQ depicts a real-time plot of the data and exports a text file of approximately 10-80 MB (corresponding to 30-120 sec runs) for post-analysis, such as using MathWorks' MATLAB programming environment.

One of significant application of the analyzer described herein is the multiplex diagnostic assays based on for example either nucleic acid or antibody-based probes. Such assays can be used for genetic screening, cancer testing, determination of A1C antigen levels, identification of various infectious diseases, or the like. The overall concept of the analyzer is to poll the population of tabs or chips in a specific assay by rotating or otherwise stochastically sampling a vessel in front of a dedicated optical detector, and observing signals from the moving and tumbling tabs or chips. A useful embodiment is to use MTPs (FIG. 1) (also known as microtransponders), which are very small silicon RFID devices to which biological probes have been attached. Each MTP contains in its memory a unique serial number (ID) that is transmitted only when relatively directly illuminated by the laser. At the same time, binding of the target is monitored using standard optical detection such as fluorescence detection. The identity of a target is deduced by correlating the ID of a MTP that "lights up" with the assay results. This technique is differentiated from particle assays that are currently the basis of multiplex testing in that each MTP has a unique electronic ID that is transmitted only when it is in the focal point of the laser, and these alignments generated in a random manner by flow, rotation, or the like. The concept for the analyzer is powerful since it enables simple "one-tube-one-step" multiplex ELISA-type or DNA-based assays, or other solid-phase assays. It has the added potential of enabling assays at high multiplex levels (e.g., 100s of targets), as well as other applications such as combinatorial chemical synthesis in drug discovery.

The compelling features of this approach are the overall simplification of multiplex assays that use flow-based platforms for fluorescent particles and the streamlining of the design, construction and maintenance of systems that have to accurately control the flow of the assay components. The novel platform can facilitate widespread distribution of assays from research and industrial diagnostic laboratories to point-of-care settings such as doctor's offices and small clinics. The platform provides high portability and field use.

Stochastic Process

The invention operates because, with a suitable selection of the vessel, the load of tabs, tab size and shape, and e.g. rotational velocity, it has been found that all, or nearly all tabs align to appropriately intersect with the light (e.g., collimated light) so as to elicit (trigger) in sufficiently close timing to associate the identifier and the analytical signal. Thus, the signal can be associated with the identified tab. Accordingly, if tab A is for analyzing hormone A, and tab B is for analyzing hormone B, one can find and distinguish the A result and B result. Where with the particular configuration, for example, one can reliably sample 80% of the tabs in a designated period of time appropriate for the assay, the vessel can contain redundant tabs sufficient to assure full sampling.

The analyzer of the invention moves tabs into alignment for reading the IDs and the analytical signal, and samples a useful population of the tabs by a stochastic process. That is to say that there is no deliberate ordering—not even so much as assuring that a random progression of tabs will linearly flow into a region for ID and signal reading. (In this latter case, the tabs are ordered in that each goes through the detection zone individually and sequentially.)

As illustrated herein, the stochastic process can be created by rotating, or by rotating and translating the sample vessel until a useful sampling of tabs has aligned for ID and analytical reading. A useful sampling is sufficient sampling so that, given the redundancies of the tabs for a particular analytical reading, all analytical readings are made. For example, if the sample vessel has 3 tabs for each analytical determination (e.g., three tabs coated with a given subject's sera), then the stochastic process reads a tab for each subjects sera. In certain embodiments, the stochastic process reads 10 or more, or 20 or more, or 30 or more, or 100 or more, or 200 or more non-redundant tabs.

Those of skill will recognize that additional mechanisms can yield the stochastic process. For example, vortexing, sonic or ultrasonic disturbance, translating back and forth, rotating, rotating and counter-rotating, see-sawing (teeter-tottering), see-sawing and translating back and forth, the rotation of a helical sample vessel, other auger-like methods of moving tabs, inducing flow within the vessel (such as with magnetic impellers), the stochastic processes described herein conducted at any angle, and the like.

Figure 18:
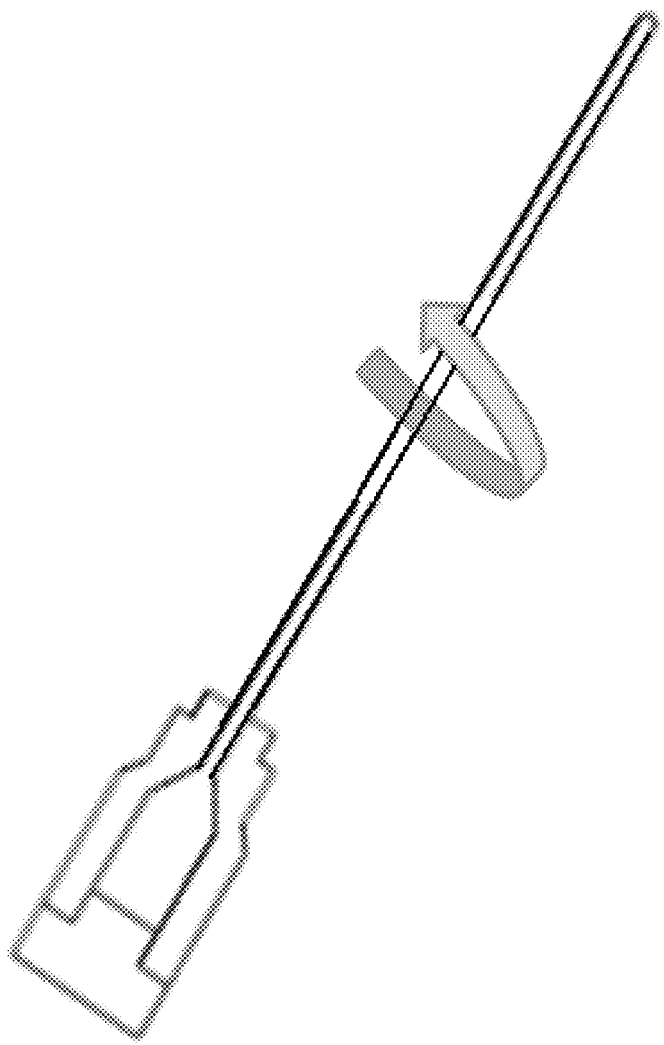
FIG. 18 illustrates an embodiment in which the sample vessel is oriented and rotated at an angle offset from horizontal.

Illustrated in FIG. 18 is a sample vessel that is offset from horizontal and rotated. Here, gravity plays a role in the stochastic process, as there can be tumbling and falling into the gravity well.

In the rotating helix sample vessel, the rotation can be adapted to keep all or most of the tabs in a common 360° loop. In this embodiment, the gravity-driven fall-back into the well of the loop provides lateral movement. These types of devices can function like Archimedes's screw. The screw action can be periodically reversed so that the tabs remain in the vicinity of detection elements, or the detection elements can move with the zone of the tabs. Circular action can provide the advantageous railing discussed below.

The sample tube (or "vessel") can be closed, meaning that during operation of the analyzer there is no source of new tabs or new bathing fluid.

The invention does not utilize (except perhaps in ancillary measurements) the process of causing tabs to flow such that they will generally pass a measurement window individually.

In certain embodiments, 80% or more of the tabs are read within 20 seconds.

For different sized or shaped tabs, for example, other parameters can be varied so as to provide sufficient sampling.

Tabs that are Light-Activated MTPs

MTPs are generally sided, in that the photocell/RF circuitry is formed on one face, and the other major face is generally silicon—and can be a product of height reduction by back grinding. The circuitry face is generally protected by a passivation layer, such as of silicon dioxide, silicon nitride or mixtures, or multiple such layers.

A MTP has a length, width and height (FIG. 1). A planar MTP is one where the height is 50% or less than the smallest of the length or width. In some embodiments, the height is 40% or less, 35% or less, 30% or less, 25% or less, or 20% or less, than the smallest of the length or width. MTPs used in the invention are often, but not necessarily, square or rectangular, consistent with a focus on low cost of production. A MTP is one where the longest of the length or width is 1.2 mm or less. In some embodiment, the longest of the length or width is 1.1 mm or less, 1.0 mm or less, 0.9 mm or less, 0.8 mm or less, 0.7 mm or less, or 0.6 mm or less. or 0.5 mm or less, or 0.4 mm or less, or 0.3 mm or less, or 0.25 mm or less, or 0.2 mm or less, or 0.15 mm or less. In one embodiment, the microchip is 600 micron×600 micron×100 or 120 micron.

Tab Features, Other Tabs, Misc.

The tabs used in the invention have an analytical surface adapted to yield a light responsive analytical signal, such as light absorption or emission. The tabs have an associated identifier, such as 1-dimensional or 2-dimensional bar code (i.e., shape-dependent identifying code), where the association is such that if a focused light beam triggers the light responsive analytical signal, reading the identifier aligned with the light beam will provide for the tab identity. In certain embodiments, the light beam illuminates or triggers the identifier.

The analytical surface can have incorporated an antibody, antibody analog, nucleic acid or the like, namely a compound that provides selectivity such that separate things can be monitored in a shared reaction vessel. It can be that in certain embodiments that the analytical surface can be adapted to retain or react with a class of molecules, such that these molecules can be picked up, or their indicative reaction products formed, in separate incubations with samples, and the molecules or their indicative reaction products are processed on the tabs in a shared reaction vessel for final reading.

Because of the ease of taking readings from the tabs with the vessel, the tabs can be separately processed, or processed in sub-pools, then consolidated into the analytical vessel.

Where joint analytical processing is conducted in at least the last step(s) of an analysis, the analytical vessel is a reaction vessel.

Identifier elements on a tab can be placed so that identification is highly correlated to sufficient alignment that the analytical signal will be generated when the identifier is triggered. For example, barcode elements (redundant elements, or separate elements needed to complete the code) can be placed on both sides of an analytical surface, such that the identifier is not triggered unless the analytical surface is appropriately framed.

The identifier such as a bar code can be associated with the analytical signal by alignment, or the collimated light can be used as an aid to reading the ID. For example, the reader can require illumination from the collimated light, so that reading events only happen when tabs and collimated light sufficiently align.

It will be recognized that multiple light sources, or a fractionally split light source (equivalent to multiple light sources) can be used. These can be used with multiple detectors for the analytical signal or ID information. Where MTPs or other RFID elements are used to provide the ID, further adjustments can be made to minimize overlapping ID readouts. For example, a detailed analysis of the analog signal received by the wand can be performed, in some embodiments combined with the use of two or more receiving antennas to spatially separate the receiving signals. As alluded to elsewhere, the analytical signal can be gathered by analyzing the individual capacitors or the like of spatially-resolved receivers such as CCDs, electron-multiplying CCDs, or CMOS sensors.

It will be understood that for MTPs the light receptor and the analytical surface can favorably share a face of an MTP. However, those of skill will recognize that the detection elements can be aligned so that the controller can determine that an ID determination is coincident with an analytical measurement. I.e., that the light has triggered an MTP that is aligned with the analytical receiver.

Light

The light can for example be from a laser, laser diode, optical fiber, light aimed by a parabolic mirror, and the like. The light source can be broad spectrum or narrow spectrum, or a combination of two narrow spectrum beams. For example, the ID and the analytical signal may be generated by the same band of light, or by separate bands such that the collimated light is engineered to carry both.

Theoretical Considerations: Liquid Flow in a Rotating Cylinder

The principles of the movement of settling particles suspended in liquids inside a horizontal rotating cylinder were studied. The problem has been researched extensively by physicists [see representative publications [13-16]. Kalyankar et al. [16] used 100 μm glass microspheres in liquids of varying viscosity in a cylinder with an internal diameter of 19 mm. He observed a variety of trajectories, some of them complex and unexpected, such as fingering flow, closed small circular orbits within the cross-section of the cylinder, and bands of particles throughout the length of the cylinder. Trajectories of MTPs will likely be even more complex because of the MTPs' square cuboid shape and their propensity to "glide" in the liquid.

Figure 2:
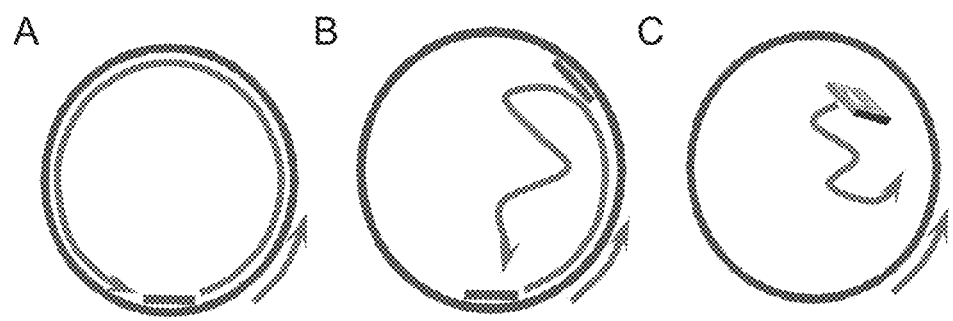
FIG. 2 shows exemplary expected trajectories of MTPs in a rotating cylinder. A: circular (corotational, "centrifuge"); B: D-shaped ("clothes dryer"); C: random (heavy mixing).

Three trajectory types (FIG. 2) for the MTP are expected:
a. circular or corotational (the MTP rests on the wall at all times; similar to centrifugation, "railing")
b. D-shaped or arch-like: the MTP resting on the wall is raised by the spinning motion of the tube half-way, and then falls to the bottom of the tube in a random way (a "clothes dryer" mode)
c. random (turbulent or chaotic, due to heavy mixing in the tube)

The movement of the tabs can be adjusted to seek to maximize arch-like trajectory (B). The fluorescence will be observed and the ID read by directing the laser beam on the central part of the arch of the trajectory. The main advantage is having the MTP oriented perpendicularly to the beam, which improves the accuracy of the fluorescence measurement and increases the likelihood of reading the ID.

Vessels

Figure 3:
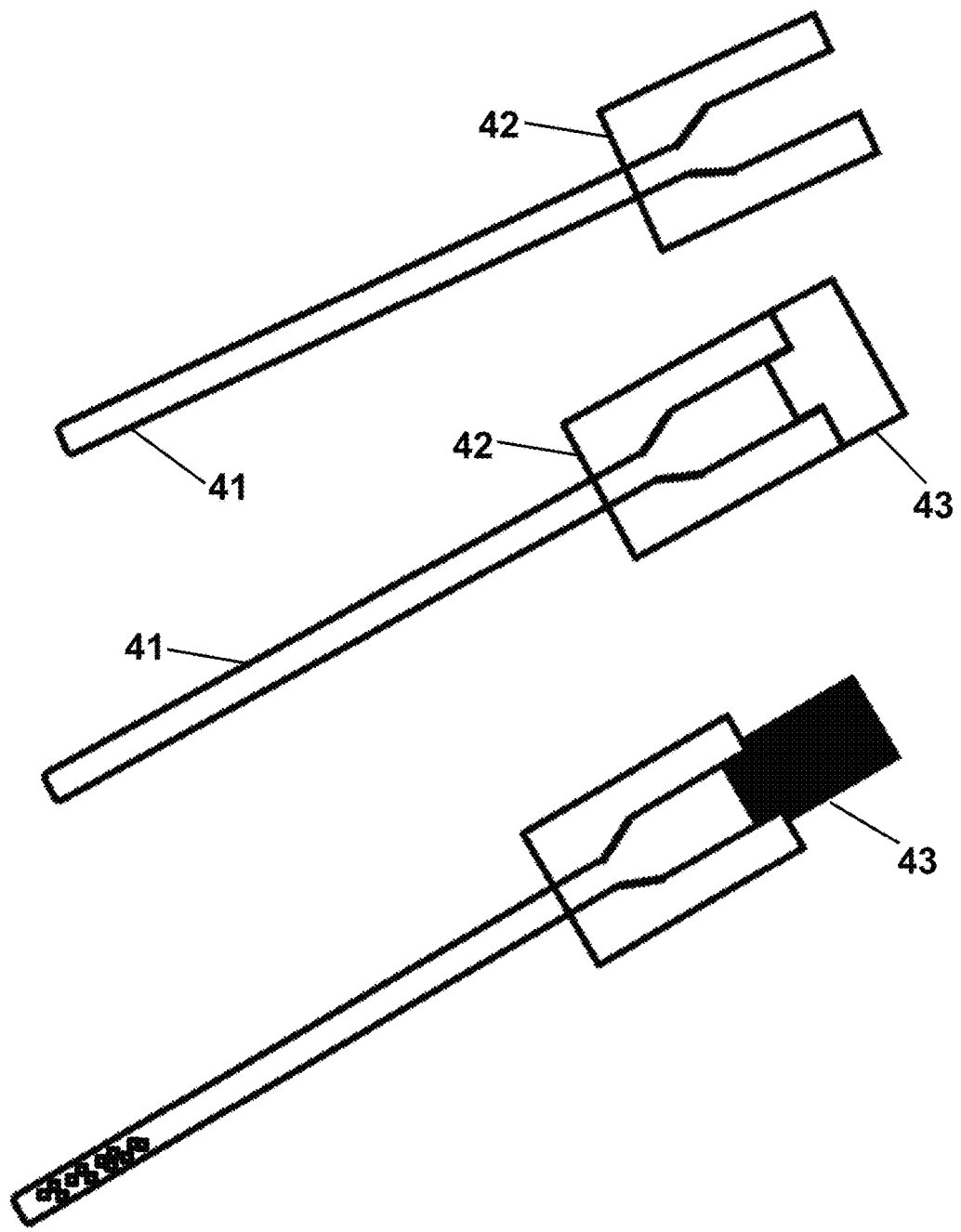
FIG. 3 shows Roche's LightCycler capillaries. Volume: 20 microliter (100 microliter versions can for example be used). From Ref. 19. (A glass capillary 41 is molded to a polypropylene reservoir 42, facilitating easy loading. A stopper 43 provides a secure seal, significantly reducing the risk of contamination.) The left panel shows three of the LightCycler vessels, one without cap, two with separate caps. The One vessel contains 45 MTPs.

The vessels can be, for example, cylindrical-like. For example, they can be cylindrical along a primary axis, with translucent walls. Where the walls along the primary axis are not round (e.g., octagonal), it may be appropriate to gate to read the identifiers and signals while the vessel sides are relatively perpendicular to the collimated light. Less strictly circular walls can influence the randomization of the alignment of the tabs. An example of a possible vessel is shown in FIG. 3.

Vessel size and shape can be selected with a number of values in mind. As practical, a size that provides a dense packing of tabs minimizes other consumables that may be needed for an assay. At the same time, a density that, for a given vessel shape, provides for too many occurrences of concurrent reads (at single detection module), or provides for too much shielding such that a sufficient percentage of tabs is not sampled in a useful time period, should be avoided.

Light-Responsive Analytical Signal

In certain embodiments, the light-responsive signal is a fluorescent signal. In certain embodiments, the light-responsive signal is an optical density, or a surrogate for an optical density.

The signal can be collected at an angle from the collimated light, which can help analytically separate a response from the stronger triggering light. In certain embodiments, it can be collected at an angle separate from 180° from the triggering light. In certain embodiments, a wavelength selective mirror is used so that light from the light source is reflected towards the vessel, and responsive light is measured after it passes directly through the same mirror.

In certain embodiments, the signal is collected in a spatially-resolved receiver, such as a 2D optical sensor such as a CCD. Color filtering elements in the sensor can help distinguish the sought-for signal.

Stochastic Reader

In certain embodiments, the analyzer lacks or does not use the second receiver. Such a device is a "stochastic reader." The tabs are read without making any reading of a corresponding analytical result. A useful embodiment of this stochastic reader uses the angled orientation of FIG. 18.

This reader embodiment can be used with robotic or cell-sorter based methods for separating tabs with negative or positive results in an analytical assay on the surface. Positive or negative tabs can be identified in the stochastic reader.

The stochastic reader can be used for inventory control. For example, tabs can be given IDs while associated for example with a larger silicon wafer. Given the size, it may be difficult to place a given set of IDs in a sales lot. With the reader, the IDs of a weight of tabs equaling say 100 tabs can be inventoried.

Illustrative Wand for Incorporation into Cyclone Analyzer

Figure 4:
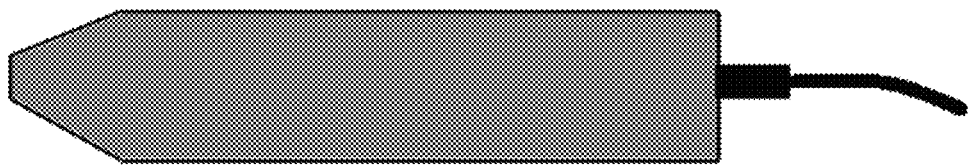
FIG. 4 is a wand and FIG. 5 illustrates principles of its design.
Figure 5:
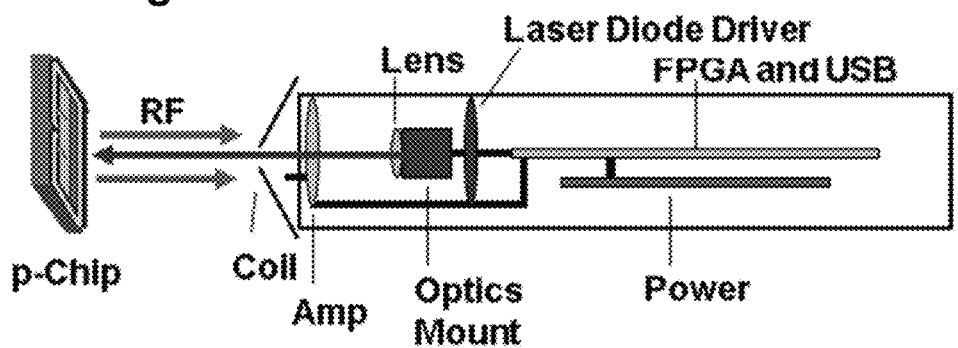

The illustrative wand (ID reader) of FIG. 4 is a hand-held device that can connect to a standard PC and is capable of reading the serial number (ID) of individual MTPs. The wand can be, for example, USB-powered and contain a USB 2.0 transceiver microcontroller, a field programmable gate array (FPGA), power converters and regulators, a laser diode with programmable current driver, an optical collimation/focusing module, and a tuned air coil pickup with a high gain, low noise differential RF receiver with hysteretic comparator data slicer. A FPGA code in the ID reader can be upgraded to support incorporation of new features and performance enhancements. The wand contains for example a laser, for example emitting an average of 60 mW of optical power at 658 nm. The ID is read when the MTP is placed within suitable proximity of and orientation to the laser light. The light can be, for example, pulsed at 1 MHz; this feature can provide the data clock used by the MTP for synchronization of the transmitted ID data bits. The timing of the pulse groups can be set so that the duty cycles and average power levels fall within requirements for registration as a Class 3R laser device (see www.iec.ch/cgi-bin/procgi.pl/www/iecwww.p?wwwlang=english&wwwprog=cat-det.p&progdb=db1&wartnum=37864).

The resulting ID readout from the MTP can be rapid (less than 0.01 sec) and can be reported on for example a PC using application-specific software and connected, through software, to an inventory database(s). A performance parameter of the wand is its read volume; i.e., the space beyond its tip in which the ID can be read. This volume is a function of several variables, including illumination angle, illuminance energy, attenuation factors and tuning of the optical system's focal point. For example, it can be approximately 6 mm3 (4 mm×1.5 mm×1 mm).

Electrical Design for ID Reader for Cyclone Analyzer

The clock signal from the laser can provide the carrier frequency used for emission of the serial ID number, therefore, the ID reader can house a laser power source. To recover the alternating magnetic field emissions from the MTP, a suitable coil that is made resonant at the operating frequency can be used so as to maximize recovered signal voltage and reject out-of-band emissions. A low-noise differential amplifier can provide gain with a high degree of common-mode rejection in order to preserve signal-to-noise ratio; the signal can then proceed for example to a voltage comparator. The binary sliced signal is then applied for example to a parallel processing decode engine realized in a field programmable gate array (FPGA). The decoder applies for example pattern-matching techniques to recognize elements of the incoming bitstream and extract the serial ID value. These signal tokens are then passed along to the host microprocessor, for example via a USB interface, for capture and presentation to the user. A safety switch can be used to inhibit laser operation in the absence of a vial to extend the life of the wand, and improve operational safety.

MTP Features

Conventional, passive RFID tags harvest power from the driving RF signal using antenna coils that are typically many centimeters in diameter. This setup results in up to approximately 1% efficiency of power transfer to the RFID device. In the case of those RFID methods that do not use such a large external antenna (such as the Hitachi mu-chip, now withdrawn from the market), the antenna efficiency drops by orders of magnitude, severely curtailing range and efficacy. Light energy harvested by photodiodes in the MTPs results in up to 10% efficiency in power transfer. Thus, because light-powered MTPs use energy more efficiently, they can achieve greater transmission ranges for the given small antenna size relative to pure RFID-based approaches. No other solution is smaller and more energy efficient.

Further, the method of powering each MTP by a tightly focused light beam (e.g., laser) allows specificity of physical addressing, i.e., addressing a dense array of tags in close proximity one tag at a time. Using traditional RFID methods, multiple tags in close proximity will attempt to communicate simultaneously, mutually interfering with one another and preventing reading of the tags. This phenomenon is known as "RFID tag collision." An RF signal is only emitted from MTPs that are activated by the laser allowing precise positional specificity.

MTP features enable a high level of security. While some RFID technologies enable additional information content, MTPs are conveniently made to contain only an ID number. All other information related to the sample container can be stored in a secure database. Thus, nothing about the sample can be determined from the physical sample container itself. In addition, the benefits of the small form factor of the MTP antenna limits transmission range to for example less than 1 cm, so that unintended transmissions are not likely.

Since triggering the MTP is alignment dependent, it is very well suited for use in the current invention.

Alignment Issues for the Analytical Signal

It can be anticipated that the alignment of the illuminated tabs with the collimated light and with the analytical receiver will yield variations in the color yield associated with the identified tab. In certain embodiments, where one seeks a signal or "no signal" answer from the analytical assay, this alignment issue will not be of particular significance. In others it can be controlled by statistical sampling, with the controller acting on the sample data to interpolate an estimated color yield. In others, the alignment can be measured, such as photographically or by radar, so the controller can calculate an alignment correction. In others, the side of the tab with the analytical surface can be colored or patterned as read at a wavelength typically different from that used for the analytical signal, to provide a control color yield or shape distortion, used by the controller to correct the analytical color yield. The components providing analytical signal itself can be patterned, so that the distortion in the pattern can be used to correct for alignment.

Where the ID receiver is a bar code reader, the controller can, as part of reading the bar code, interpret the degree of angular distortion of the bar code to deduce the alignment of the tab.

Where the analytical signal receiver is a spatially-resolved receiver (such as a CCD), the distribution and amplitude of signal across the receiver can be used to correct for, or partially correct for, signal reductions due to alignment.

Where arch-like trajectories are sufficiently achieved, alignment issues are minimized, since the tab will be aligned against the side of the sample vessel.

Associating the Analytical Signal and the ID

With MTPs, the analytical surface can be placed such that a triggering of the radio signal identifier will happen if and when the collimated light is aligned with the analytical surface. As outlined above, the two events can be made co-dependent when using other identifier systems.

The analytical signal derives from the collimated light being sufficiently aligned with the analytical surface of a tab. Where the tab is a MTP, ID data signal is emitted as a result of roughly the same alignment, and degree of temporal concurrence between the ID data signal and the analytical data can be established empirically, or via modeling, or the like.

Where the ID data is for example a bar code, bar code reading can be done along the same optical path as used for the collimated light. As such, bar codes will be identified in rough concurrence with analytical signal, such that sufficient temporal concurrence between the ID data signal and the analytical data can be established empirically, or via modeling, or the like.

Controller for Analyzer

Figure 13:
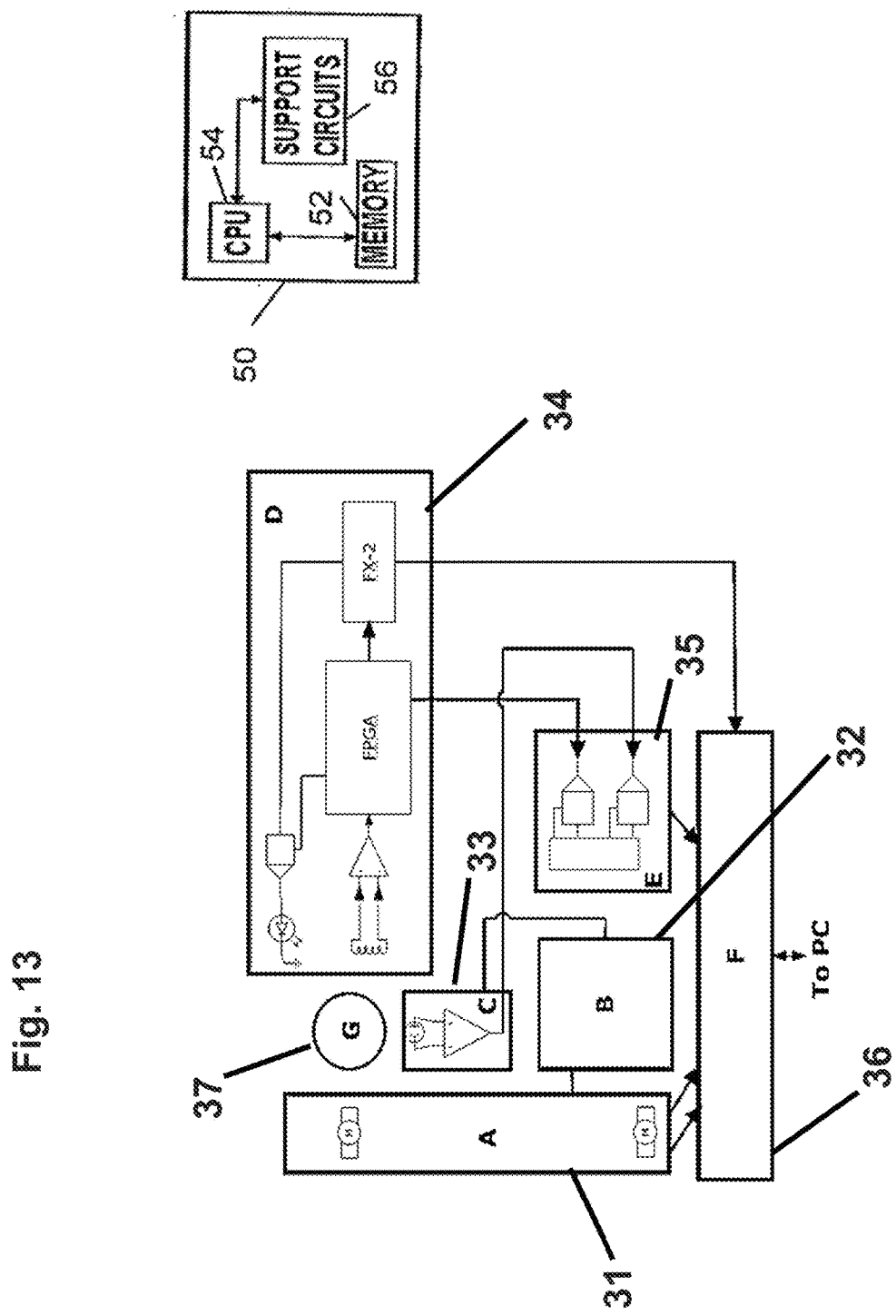
FIG. 13 provides a schematic of exemplary electrical system in the analyzer. 31: servo motors and controller; 32: power supplies (−12,12 VDC); 33: photomultiplier tube assembly; 34: ID reader; 35: USB DAQ module; 36: 4-port USB hub; 37: location of test vessel.

The analyzer has controller 50 (FIG. 13), which can comprise a central processing unit (CPU) 54, a memory 52, and support circuits 56 for the CPU 54 and is coupled to and controls the analyzer or, alternatively, operates to do so in conjunction with computers (or controllers) connected to the analyzer. For example, another electronic device can supply software, or operations may be calculated off-site with controller 50 coordinating off-sight operations with the local environment. The controller 50 may be one of any form of general-purpose computer processor, or an array of processors, that can be used for controlling various devices and sub-processors. The memory, or computer-readable medium, 52 of the CPU 54 may be one or more of readily available memory such as random access memory (RAM), read only memory (ROM), flash memory, floppy disk, hard disk, or any other form of digital storage, local or remote. The support circuits 56 are coupled to the CPU 54 for supporting the processor in a conventional manner. These circuits can include cache, power supplies, clock circuits, input/output circuitry and subsystems, and the like. Methods of operating the analyzer may be stored in the memory 52 as software routine that may be executed or invoked to control the operation of the immunization testing device 100. The software routine may also be stored and/or executed by a second CPU (not shown) that is remotely located from the hardware being controlled by the CPU 54. While the above discussion may speak of the "controller" taking certain actions, it will be recognized that it may take such action in conjunction with connected devices.

All ranges recited herein include ranges therebetween, and can be inclusive or exclusive of the endpoints. Optional included ranges are from integer values therebetween (or inclusive of one original endpoint), at the order of magnitude recited or the next smaller order of magnitude. For example, if the lower range value is 0.2, optional included endpoints can be 0.3, 0.4, . . . 1.1, 1.2, and the like, as well as 1, 2, 3 and the like; if the higher range is 8, optional included endpoints can be 7, 6, and the like, as well as 7.9, 7.8, and the like. One-sided boundaries, such as 3 or more, similarly include consistent boundaries (or ranges) starting at integer values at the recited order of magnitude or one lower. For example, 3 or more includes 4 or more, or 3.1 or more.

EXEMPLARY ANALYSES

Example 1

The principles of the movement of settling particles suspended in liquids inside a horizontal rotating cylinder were studied. Physicists have researched this problem extensively (see representative publications [15-18]). Kalyankar et al. [18] used 100 μm glass microspheres in liquids of varying viscosity in a cylinder with an internal diameter of 19 mm. They observed a variety of trajectories, some of them complex and unexpected; such as fingering flow, closed small circular orbits within the cross-section of the cylinder, and bands of particles throughout the length of the cylinder. Trajectories of MTPs are expected to be even more complex because of the MTPs' square cuboid shape and their propensity to "glide" in the liquid.

Up to 50 MTPs in Roche LightCycler 100 microliter capillary vials (Ø2.25 mm, L=35.25 mm) [19], which we note, are manufactured specifically for fluorescence detection applications, were used. Vials were filled with either H2O or buffer (phosphate-buffered saline, Tris-buffered saline). Several vial orientations were studied, and we concluded that the most predictable and controllable orientation is when the axis of the vial is horizontal.

The trajectory of the chips can be grouped into three basic modes: (1) no/little activity: MTPs remain on the bottom of the vial, moving only slightly back and forth (FIG. 15A); (2) tumbling: MTPs are raised on the wall by the spinning motion of the vial, but fall back to the bottom in a random manner partway through a full rotation like in a "clothes dryer" (FIG. 15B); and (3) railing: MTP rest on the wall moving co-rotationally with the vial, similar to centrifugation (FIG. 15C). One special case is a "D-flip" mode: MTPs rail on the side of the vial until reaching the top, then vial rotation is stopped, and the MTPs glide down evenly (FIG. 15D). In addition, MTPs that start at rest clustered at the domed-end of a horizontal vial have been observed to spread out along the length of the vial when rotated.

The focus of the experimentation was to combine these modes of activity to effectively manipulate MTPs for optimal and efficient data collection. It was determined that MTPs can be spaced out from each other to limit detecting fluorescence from neighboring MTPs. The laser beam was directed orthogonal to the tangent plane of the vial at the 90° orientation (see FIG. 15A for orientation angle reference). As the vial rotates and the MTPs carried up the wall, their orientation remains orthogonal to the beam, thus minimizing variation over multiple measurements per chip and increasing the probability of reading the ID.

A useful flow and detection procedure for a run time of about 90 seconds is as follows: (1) spread chips across vial, (2) rail chips, (3) scan vial utilizing a horizontal movement drive from one end (e.g. domed-end) to other, (4) scan vial in the reverse direction, (5) tumble chips, and (6) repeat steps 2-5 as desired.

Example 2. Probability Calculation of Reading Tabs

The problem of reading MTP IDs on the Spinner or Cyclone can be formulated as follows:

MTP IDs are in the range from 1 to n. The MTPs are mixed in a vial. The chips are presented randomly to the reader, and the IDs read r times. What is the probability P that exactly N different IDs are read (r≥N)?

The solution is given by the equation below:

$$P = \sum_{k=0}^{N} (-1)^k \binom{N}{k} \left(1 - \frac{k}{n}\right)^r$$

The source of the above formula is this book: William Feller, Introduction to Probability Theory and Its Applications, Volume 1 Second Edition, John Wiley and Sons Publishers, New York, 1961. See: Chapter IV, Section 6, Problem 8.

Figure 6:
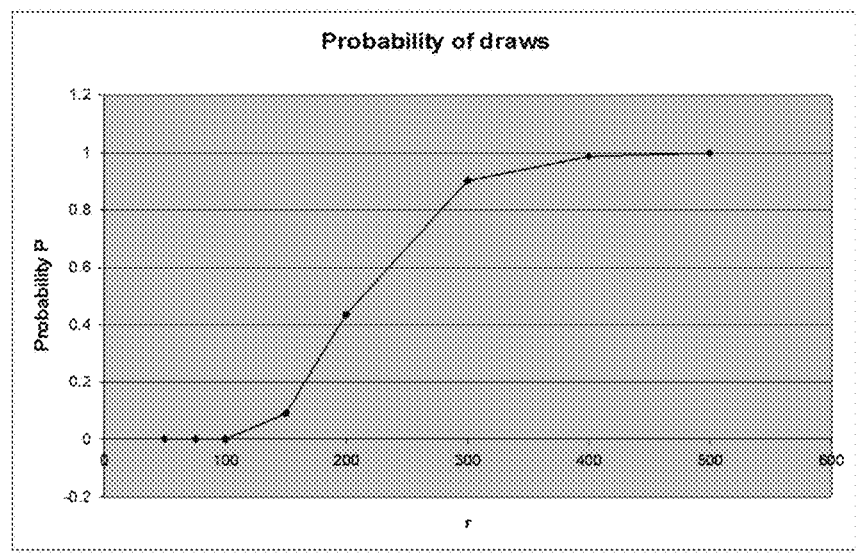
FIG. 6 provides calculations of probabilities of drawing tabs.

A calculation was done in Excel for the following set of parameters: n=50, N=45, r=400. The results are plotted as linear and semi-log plots in FIG. 6.

Example 2. Time Course Simulation for Reading Tabs

Figure 7:
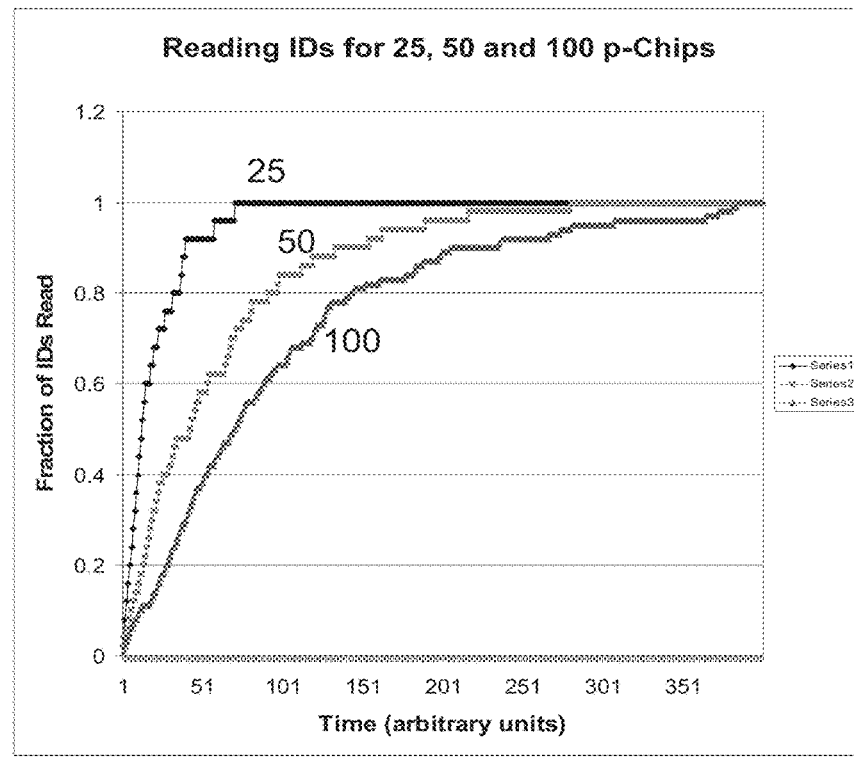
FIG. 7 provides a simulation of the time course of reading the IDs.

The time course of reading the IDs was simulated in Excel. The results are presented in two graphs in FIG. 7. The difference between the graphs is the coordinate system. The time needed to read an ID corresponds to one unit on the x-axis. The analysis shows that the semi-log plot of the fraction of unread IDs approximates a straight line.

Example 3. Prototype #1 of the Analyzer

A prototype of the analyzer is shown in FIG. 8. It is composed of a mechanical system for rotating the sample tube, an optical system and electronics. The optical system includes a 660 nm single-mode laser diode (Hitachi Opnext HL6545MG) focused 40 mm from the filter cube output window by a Thorlabs A230TM-B aspheric lens (f=4.51 mm, NA=0.54). The custom filter cube consists of Ø6 mm emission and excitation filters, Semrock FF01-661/11 and FF01-692/LP, respectively, and a 7 mm×10 mm Semrock FF677-Di01 dichroic beam splitter. A pick-up coil is located at the filter cube output window. The sample is contained in a polypropylene vial (Worldwide Medical Products BioExcell 0.1 mL Strip Tube, P/N 41011000) located 2-3 mm from the filter cube output window. MTPs within the vial are suspended in aqueous liquid, preferably void of an air gap. A photomultiplier tube (PMT) (Hamamatsu H5784-20), coupled to the filter cube with an overall path length of 35 mm from the vial, measures fluorescence intensity.

The mechanical system includes two stepper motors mounted on a 18" by 24" breadboard to provide translational and rotational degrees of freedom. The electronic controls of a commercial PharmaSeq ID reader (Pharmaseq, Monmouth Jct., N.J.) were used to acquire MTP IDs.

Data was collected using a USB DAQ data acquisition device (Measurement Computing USB-1608FS). This device samples data streams (fluorescence and IDs) at a rate of 40 kHz per channel with 16-bit resolution. The Measurement Computing Universal Library API (specifically the .NET binding of this library) was used to control the Analyzer. The software implementation was written in C#.NET for the Microsoft .NET 4.0 platform. The data was stored to disk as large (~10 MB for a 30 sec capture) text files. The files were then imported into MATLAB for post-analysis.

Results and Characterization. Initial testing was performed on a single MTP glued in a fixed position in a vial rotated at 50-350 rpm. Tests were performed to calibrate the system, devise data-syncing criteria, and assess the extent of signal processing required for fluorescence measurements. The next step was to glue three MTPs labeled with Cy5.5 fluorophore in a ring inside a vial. FIG. 10 shows a representative fluorescence profile from the test. A noise filtering algorithm was used to detect peaks, and a data-syncing algorithm was used to associate peaks to IDs.

The results were quite good: distinct well-resolved fluorescence peaks and readouts of IDs are observed at appropriate times. Undesired peaks in FIG. 10 are attributed to the three MTPs presented to the laser beam on the far side of the vial. The IDs are not read as effectively at that distance and in that orientation, and are therefore not associated with an ID.

Figure 11:
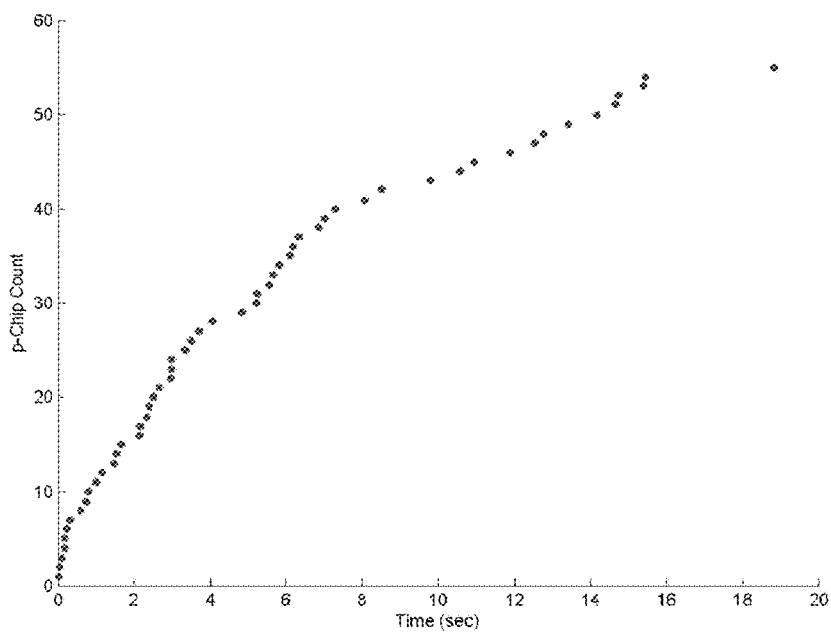
FIG. 11 provides an illustration of the acquisition of MTP IDs from the vessels harboring the MTPs. 75 MTPs suspended in distilled water in a 0.1 mL vial were rotated at 250 rpm. In 20 secs, 80% of MTP IDs were read at least once.

Another test was performed to determine how efficiently MTPs can be read in higher densities. 75 MTPs suspended in water were placed in a vial and rotated at 250 rpm. The results (FIG. 11) showed that 58 unique MTP IDs were read within 20 sec, meaning that without any optimization regarding rotational speed, read location, translation, or tilt parameters, almost 80% of MTPs were read quickly. Overall, the initial tests demonstrate overwhelmingly that fluorescence-based assays with MTPs in a rotating cylinder are feasible.

Example 4. Prototype #2 of the Analyzer

Figure 12A:
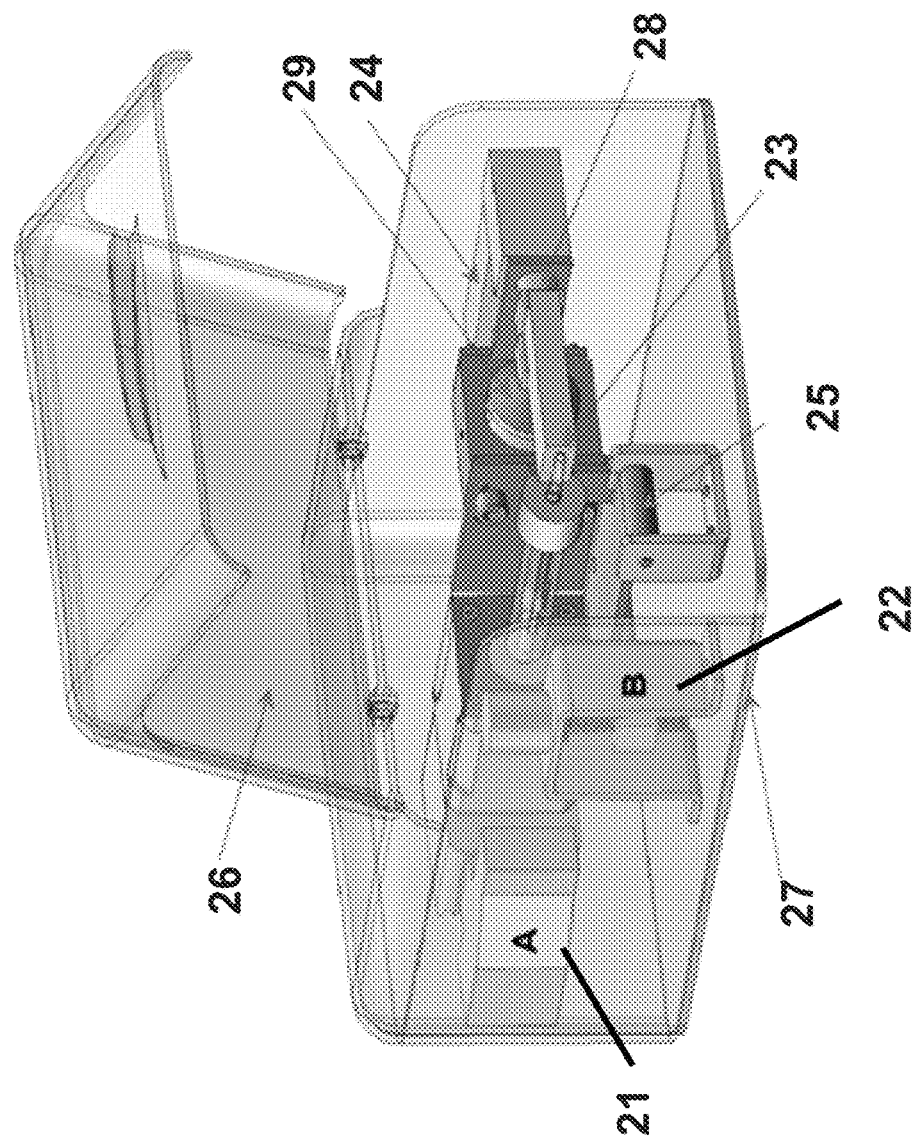
FIG. 12A provides an exemplary mechanical design of the analyzer. The key components are: 21: Main servo motor/controller; 22: tilt adjustment servo; 23: sample vessel; 24: photomultiplier tube; 25. hinge support; 26: lid; 27: baseplate; 28: optics assembly; 29: ID reader.
Figure 12B:
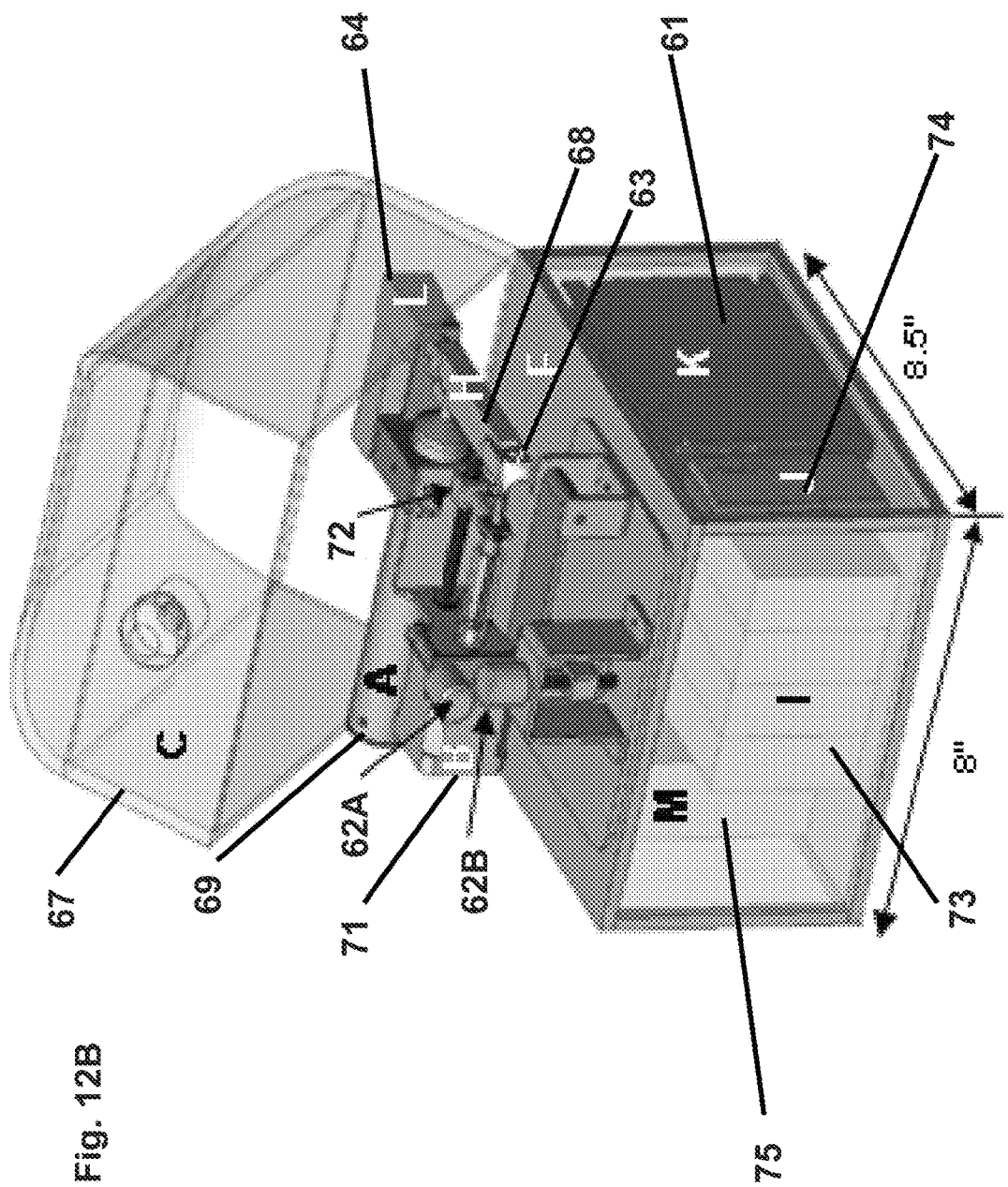
FIG. 12B provides an exemplary mechanical design of the analyzer. The key components are: 69: ID reader; 71: rotational stepper motor; 67: lid; 62A: Y-tilt adjustment servo; 62B: X-tilt adjustment servo; 63: sample vessel; 72: linear (translational) adjustment servo; 68: optics assembly; 73: motor drivers; 74: USB hub; 61: motor controller; 64: photomultiplier tube; 75: power supply.

Design principles. An overall design is presented schematically in FIG. 12A (as well as in FIG. 12B). The prototype will be a small portable unit on a breadboard with a protective cover. The dimensions are 9×8.5×3 inches, far smaller than conventional flow-based instruments. The electrical power can be provided by an external AC/DC charger. The fluorescence detection system can be similar to that in the above demonstration system. The wand components can be taken out from the round wand enclosure and properly arranged in the box. Data can be transmitted via USB in a format similar to the current format for the Pharmaseq Tsunami 5 device. A choice of wavelength can be made between 532 or 650 nm. A two (or more) color system can be considered. The sample tube can be the glass capillary used in the Roche's LightCycler qPCR instrument (FIG. 3), or custom built, in which case the diameter can for example be about 5 mm and the length 20-50 mm (about 39 to about 98 microliter). The on-board analog to digital conversion (ADC) can take place via a daughter board interfaced directly to an ID reader's FPGA.

The work is facilitated by recordings of the movement of the MTPs in the sample tube with a high-speed camera (such as Redlake MotionScope 8000 S) at rates up to 8,000 frames per sec.

Optical system to measure fluorescence intensity. The optical system can be similar to the above described demonstration system. A primary adjustment can be to reshape the laser beam to suit the small radius of curvature of the vial. Corrections can be introduced to compensate for different factors:

- position and angular orientation of the MTP along optical path
- almost simultaneous reading of fluorescence from two or more MTP present at the same time along the optical path
- background caused by the scattered excitation light, inducing fluorescence from other MTPs Proper fluid selection (including viscosity) can be based on modeling MTP trajectories in a rotating cylinder. With that information, and after determining a high efficiency position around the vial where measurements can be taken, optics modeling of excitation and emission photons can dictate the selection of excitation beam profile, as well as what type of collection optics would be effective, such as: (1) custom filters designed around larger incident beam cone angles, (2) cylindrical condenser, possibly bifocal, between the filter cube and vial, or (3) an array sensor to capture large emission angles. An optical method in which to account for variations in MTP orientation/position could be the use of a second photon detector to measure reflection from the MTP.

Mechanical system to move the tube. The intended functions include the rotation of the sample tube, lateral motion, and tilt adjustment. A small stepper motor can be used. When the stepper motor runs, a nut fixed on the mounting frame forces the driving screw to move along the axis of rotation, varying the tube's position. Therefore, a sleeve works as a drive coupling providing linear motion. Reversal of the rotational direction causes linear motion of this coupling in the opposite direction. All components can for example be mounted on one frame, which can provide tilt adjustment without changing the relative positions between the constituent sub-elements. With the help of a hinge support and servo motor lifter system, this arrangement can vary the horizontal orientation of the sample tube during the assay. In addition, the stepper motor rotates the tube and moves the test tube to the loading and unloading position outside of the enclosure via the custom coupling device described above. The dimensions of the analyzer could for example be as small as 9×8.5×3 inches or even 6×6×2 inches if built from custom sub-elements after a dimensional optimization.

Electronics. MTPs are to be read using a conventional architecture similar to that used in existing PharmaSeq ID readers. In the ID reader, a 300-turn pickup coil is coupled to a gain controlled signal amplifier whose output is digitized to 14 bits of precision in an analog-to-digital (A/D) converter. The converter samples at 32 Msps (mega-samples per second) and provides the sampled signal data in parallel to a large FPGA (as used in the pre-commercial PharmaSeq Series 5000 ID reader) for signal processing. The Series 5000 FPGA has approximately 10 times the memory of the device currently used in PharmaSeq's ID readers, enabling more sophisticated multilevel signal processing as well ancillary control functions relevant to the instrument being described herein, such as control of the photomultiplier tube (PMT) gain and processing of PMT fluorescence signals. A 18 line expansion bus for example permits addition of external elements, such as a low speed ND converter for digitizing the fluorescence signals supplied by the sensing PMT. This converter and interface elements can be realized on a plug-in daughter card that interfaces to an existing socket on the Series 5000 mainboard.

Having the ID decode engine co-resident with fluorescence read channel processing elements enables maximal integration of functionality in the smallest possible form factor. The existing hardware provides a unified USB interface for communicating correlated ID and fluorescence data to the host PC. A switched-mode power supply is arranged for example to provide power to the PMT. The RFID and fluorescence processing elements are powered for example by USB from the host PC. A schematic of exemplary electrical circuits in presented in FIG. 13.

Mechanical enclosure. The intended functions include the protection of internal parts, isolation from light, providing mounts for internal parts, and the facility to load the test tube. The system can be designed to optimize sub-assemblies for function, space, and cost. The system is not expected to consume significant amounts of power nor emit significant amounts of heat, but adequate temperature management for reliable assay performance may be necessary. Enclosure design also requires considerations for EMI and laser safety regulations. Therefore, proper analysis through multi-physics modeling and data logging will play a major role in the overall system enclosure.

Characterizing the Analyzer's Performance. The measurement capabilities of the spin reader can be assessed based on the following criteria: (1) sensitivity to the industry-standard "low" fluorescence levels, (2) high statistical confidence on a per chip basis, and (3) amount of time required to complete a measurement.

Example 5. Bioassays

Multiplex DNA hybridization assay. A DNA-based assay for determining fifty mutations responsible for cystic fibrosis (CF) has been developed [2]. This work is now focused on preparation for clinical trials. The same group of reagents and MTPs prepared for the CF assay can be used to evaluate the performance of the new analyzer, except that the streptavidin-phycoerythrin conjugate used for staining can be replaced with a streptavidin-Cy5.5 conjugate. The primary objective is to establish how many chips can be conveniently used in a single assay. The results will be compared with the readout from the current flow reader.

Figure 15:
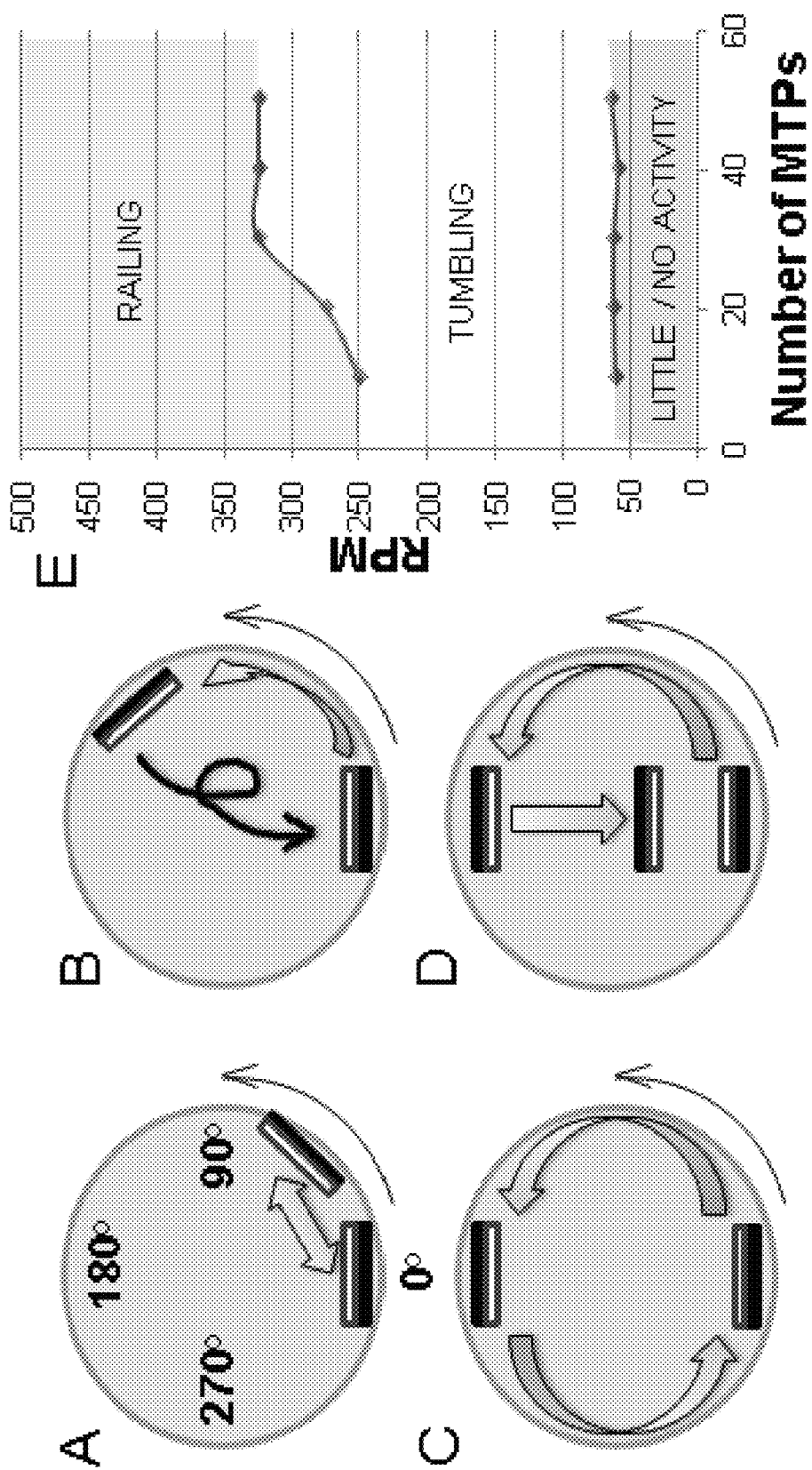
FIG. 15 is a more detailed study of MTP trajectories.

Feasibility of one-tube-one-step assay. The exemplary assay does not require washing steps to remove fluorescent label that is not bound to the molecular target. In one implementation, the tolerance to having an unbound label stems from the ability of the analyzer to read out the fluorescence emanating directly from the MTP surface as it lies on the wall of the sample tube during the readout (FIG. 15). Here, the exiting laser beam is narrow enough to illuminate only the chip. A study can be performed on a model system where have different amounts of fluorescent material on MTPs are used, and the tolerance of the system to varying concentrations of a fluorescent dye in the buffer in the sample tube is investigated. The maximum and optimal number of chips used in this assay can also be determined.

Two Assays. Two assays, a DNA hybridization and a no-wash assay, have been demonstrated. 30 MTPs were sealed in a vial and rotated at a maximum speed of 375 rpm. The full readout cycle was based on the flow procedure mentioned above. The total readout time was 80-90 sec over which 25-30 chips were interrogated. The average event time per MTP was about 30 msec.

Figure 16:
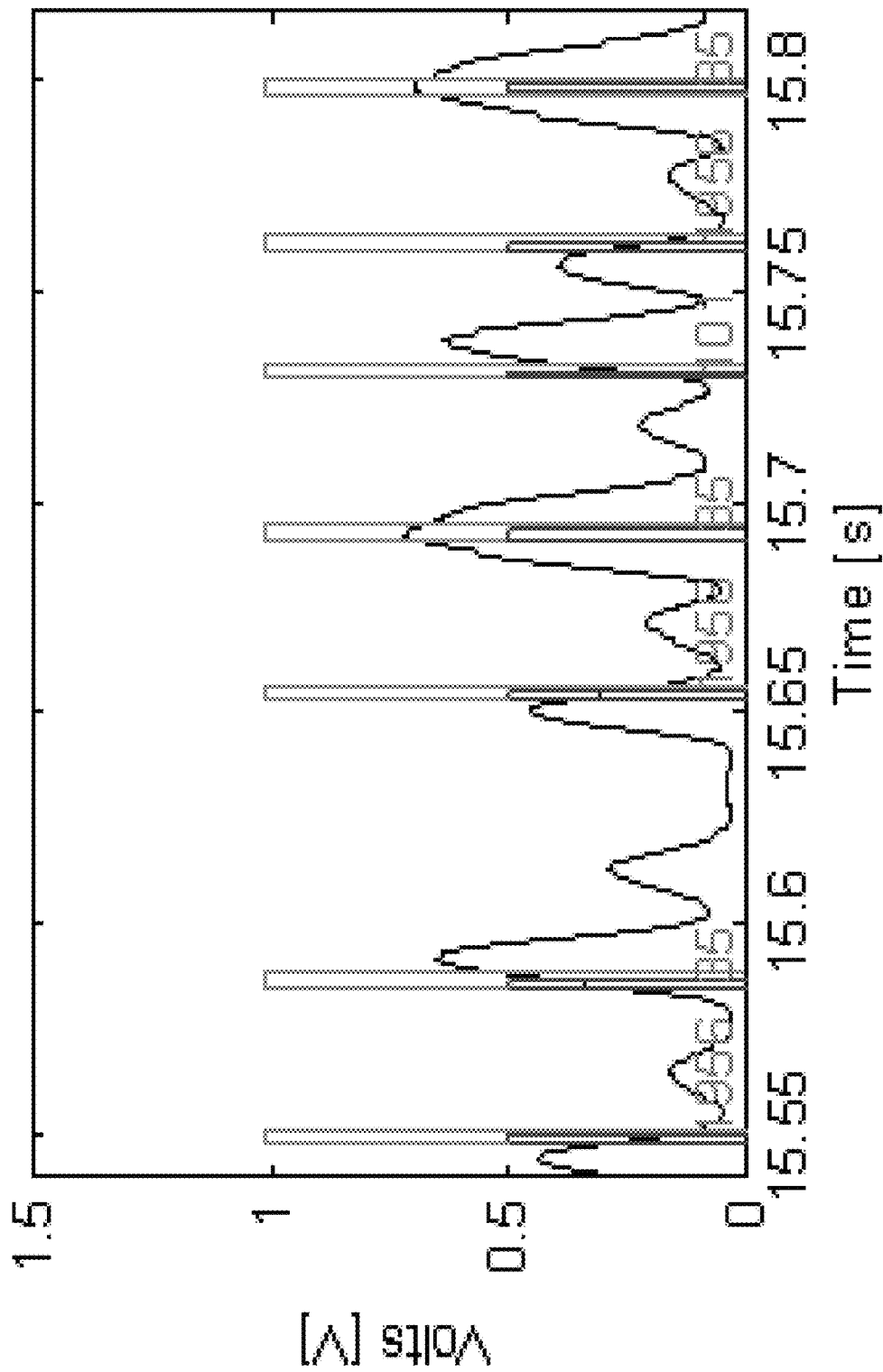
FIG. 16 provides data from a DNA hybridization assay.

DNA Hybridization. A representative fragment of a plot of the data stream is shown in FIG. 16. The y-axis shows the observed fluorescence intensity. The trace with smooth-shaped peaks is the photomultiplier tube data. The smaller bars are the decoded ID data. The larger (taller) bars are the synchronized ID data. The inset numbers are the MTP IDs.

A 33 nucleotide oligonucleotide (from a cystic fibrosis assay) was conjugated to the MTPs. A partially complementary 46 nt. biotinylated target oligonucleotide was hybridized to the MTPs. The hybridized MTPs were stained with Cy5.5-labeled streptavidin-Allophycocyanin (APC) conjugate. Incubations with different concentrations of target were conducted and pooled, yielding MTPs with different signal strengths. Then, the fluorescence and IDs of all MTPs were read in the analyzer ("Cyclone reader"). Strong fluorescence signal was obtained (FIG. 16). Fluorescence peaks without a corresponding ID in FIG. 16 typically originated from MTPs illuminated while at the 270° position (see FIG. 15A). The readout was validated against fluorescence intensities/IDs of the same MTPs read under a fluorescence microscope (data not shown). Expected reads were obtained in over 90% of the cases.

No Wash Assay. Biotinylated serum albumin was conjugated with the MTPs. The biotinylated MTPs were incubated with 200 microliters of a solution of Cy5.5-labeled streptavidin-APC conjugate for 7 days, then analyzed in the analyzer without any washes. The experiment was done in separate sample tubes with three different dilutions of Cy5.5-labeled streptavidin-APC conjugate (from 0.1 nM to 100 nM).

Figure 14:
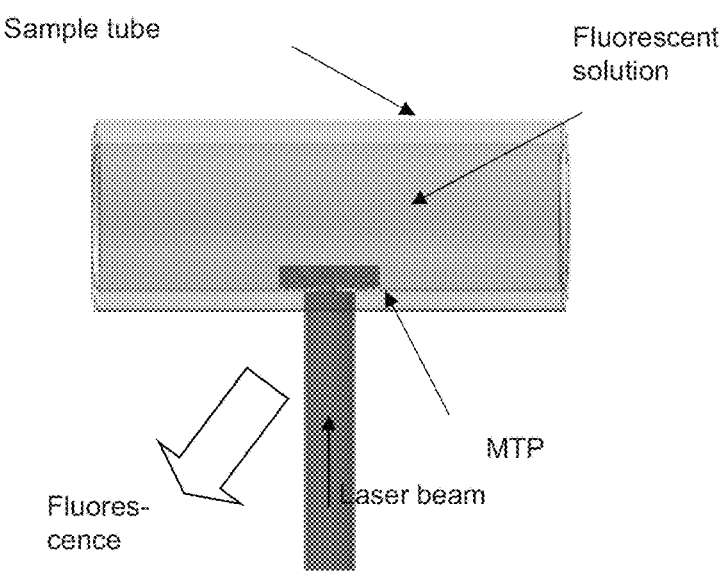
FIG. 14 illustrates a no-wash assay on MTPs. One chip only is shown for illustrative purposes. A small size of the laser beam and the on-the-wall position of the MTP eliminate acquisition of fluorescence from the solution. Drawn not to scale.
Figure 17:
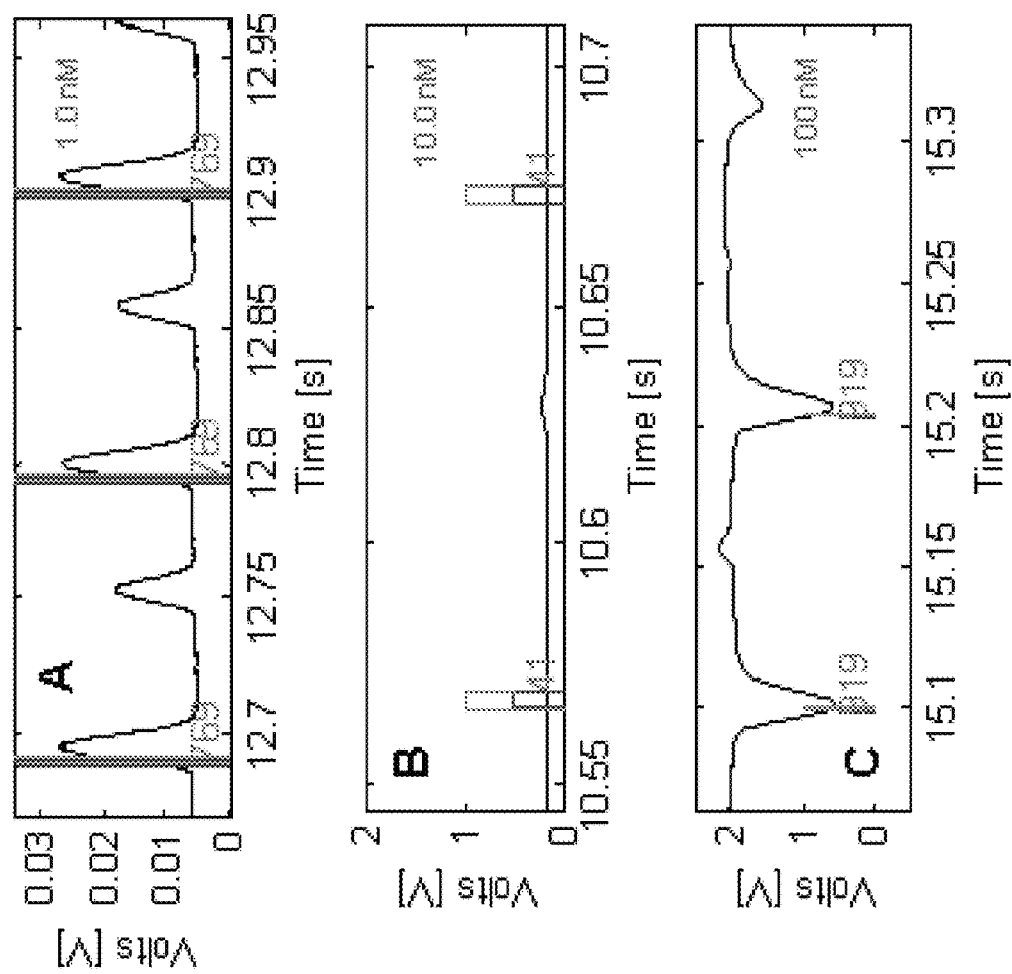
FIG. 17 shows a no-wash assay.

The no-wash concept is illustrated in FIG. 14. The results shown in FIG. 17 demonstrate acquisition of properly ascending fluorescence signals as the concentration of the analyte in the vial increases. Panel A is for 0.1 nM; Panel C is for 100 nM Cy5.5-labeled streptavidin-APC conjugate.

(Negative values are a function of the un-bound label in solution, but the negative values are capable of normalization.)

Key Advantages

No fluidics system needed: new paradigm for fluorescence readout from small particles. A well-established principle of reading the fluorescence intensity from small particles is flow fluorometry. A widespread implementation of it is the Luminex XMAP platform. According to the flow fluorometry principle, particles are moved linearly and sequentially in a capillary at a high speed through the laser beam, and fluorescence intensity (and other parameters) are recorded. This is also how the PharmaSeq flow reader ("Tsunami") operates. The disadvantage of flow-based systems is that they are expensive due to challenges of accurately controlling a flowing liquid, and they are often bulky. In contrast, the principle adopted in the current project calls for moving the sample tube containing the particles in the path of the laser beam and stochastically (statistically) sampling the particles. This greatly simplifies the design and reduces the size of the analyzer. The illustrative readout method resembles drum scanning of a MTP array formed on the wall of the moving sample tube, followed by the mixing of the chips and a reassembly of the array. If needed, a binding (or staining) reaction can be concurrent with the readout.

For example, with a 100 micrometer vessel, it is anticipated that the method of the invention can, without further optimization, sample 50-100 tabs per minute, as opposed to about 3 per minute.

Enablement of several types of assays. The analyzer can become widely adapted for in vitro diagnostics. In addition to protein or DNA-based sandwich (ELISA) assays, several types of assays will be enabled by this new platform:

One-tube-one-step assay (FIG. 14). This involves the one-tube-one-step no-wash design with MTPs as the solid phase. The no-wash feature is possible because the MTP can be read while it is resting on the wall of the sample tube and the cross-section of the laser beam is smaller than the MTP. Thus, proper fluorescence readout from the MTP surface can be made even though the concentration of fluorescent molecules in the sample tube is significant (as a result of not having a wash step). In other words, functionally the behavior resembles a homogenous assay (mixing two reagents, measuring the result from the solution), even though a solid phase is involved.

Determination of binding kinetics. Since each MTP is read multiple times during the course of the assay, measurement of binding rate constants or other rate dependent processes is enabled. This is especially applicable for the no-wash assay outlined above.

The approach can be used at two steps in split-and-mix combinatorial synthesis with analysis on MTPs. First, after the split step, the IDs of MTPs can be read in nearly any solvent. Second, after the synthesis is completed and fluorescence-based bioassay performed (which typically involves a targeted molecule), the drug-target binding interactions can be evaluated.

Current Multiplex Assays and Need for New System. Currently available multiplex assays include: (a) several bead-based assays implemented on the Luminex platform [8-10] and (b) sandwich ELISA assays formatted in the wells of a microtiter plate, such as SearchLight (Endogen), MULTI-ARRAY (MesoScale Discoveries) and FAST Quant (Schleicher & Schuell). In comparison, the MTP surface is attractive because silicon has very low fluorescence background, generally better than that of metals, polystyrene, or even glass. A particular advantage of MTPs over polystyrene beads is the possibility of tracking and archiving every individual particle during and after the assay by the unique ID each chip possesses. In addition, the flat surface is ideal for application of silver nanoparticle layers (SNL), which, by virtue of plasmon-enhanced fluorescence, can increase the reported signal by a factor of 10- to 100-fold [11-12]. Our results for an IL-6 cytokine immunoassay on MTPs have shown that SNL provides a 25-fold increase of assay sensitivity over non-SNL [3]. (See, also, WO 2011/137325.) This significant enhancement over the standard ELISA, plus the lower sample volume and favorable reaction kinetics from the efficient interaction of the MTP particles with analytes in solution, will make the PharmaSeq assay a desirable alternative to existing assays.

BIBLIOGRAPHY

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

REFERENCES

1. Lin X, Flint J, Azaro M, Coradetti T, Kopacka W, Streck D, Wang Z, Dermody J, and Mandecki W (2006) Microtransponder-based multiplex assay for genotyping cystic fibrosis. ClinChem 53: 1372-1376
2. Li J, Wang Z, Gryczynski I and Mandecki W (2010) Silver nanoparticle-enhanced fluorescence in microtransponder-based immuno- and DNA hybridization assays. Anal BioanalChem 398:1993-2001
3. Mandecki W, Ardelt B, Coradetti T, Davidowitz H, Flint J, Huang Z, Kopacka W, Lin X, Wang Z, and Darzynkiewicz Z (2006) Microtransponders, the miniature RFID electronic chips, as platforms for cell growth in cytotoxicity assays. Cytometry Part A 69A:1097-1105
4. Robinson E J H, Thomas O, Richardson T O, Sendova-Franks A B, Feinerman O, and Franks N R (2009) Radio tagging reveals the roles of corpulence, experience and social information in ant decision making. BehavEcolSociobiol 63(5) 627-636
5. Robinson E J H, Mandecki W (2011) In: Ant Colonies: Behavior in Insects. Editor: E C Sun, Nova Science Publishers, Inc. ISBN: 978-1-61122-023-0
6. Jolley-Rogers G, Yeates D K, Crost J, Cawsey E M, Suter P, Webb J, Morris R G, Qian Z, Rodriguez E and Mandecki W (2012) Ultra-small RFID p-Chips on the heads of entomological pins provide an automatic and durable means to track and label insect specimens. Zootaxa 3359: 31-42
7. Gruda M C, Pinto A, Craelius A, Davidowitz H, Kopacka W M, Li J, Qian J, Rodriguez E, Kuspiel E and Mandecki W (2010) A system for tagging laboratory mice with light-activated microtransponders. J Am Assoc Lab Anim-Sci 49:826-831
8. Ray C A, Bowsher R R, Smith W C, Devanarayan V, Willey M B, Brandt J T, Dean R A: 2005. Development, validation, and implementation of a multiplex immunoassay for the simultaneous determination of five cytokines in human serum. J Pharm Biomed Anal 36(5):1037-1044.
9. Siawaya1 J F D, Roberts T, Babb C, et al. 2008. An evaluation of commercial fluorescent bead-based Luminex cytokine assays. PLoSOne, 3(7): e2535.
10. Schneiderhan-Marra N, Kirn A, Dottinger et al. 2005. Protein microarrays—a promising tool for cancer diagnosis. Cancer Genomics & Proteomics 2: 37-42.
11. Lakowicz J R, Shen Y, D'Auria S, Malicka J, Fang J, Gryczynski Z, Gryczynski I. 2002. Radiative decay engineering. 2. Effects of silver island films on fluorescence intensity, lifetimes, and resonance energy transfer. Anal Biochem 301:261-277.
12. Gryczynski I, Matveeva E G, Sarkar P, Bharill S, Borejdo J, Mandecki W, Akopova I, Gryczynski Z. 2008. Metal enhanced fluorescence on silicon wafer substrates. ChemPhysLett 462:327-330.
13. MAGPIX Technology Technical Note "Magpix provides equivalent performance to the Luminex 100/200 in an HPV vaccination trial". Luminex (2012)
14. Baker, H. N., Murphy, R., Lopez, E., Garcia, C. (2012) Conversion of a Capture ELISA to a LuminexxMAP Assay using a Multiplex Antibody Screening Method. J. Vis. Exp. (65), e4084
15. Matson W R, Kalyankar M, Ackerson B J, Tong P (2005) Concentration and velocity patterns in a horizontal rotating suspension of non-Brownian settling particles. Phys Rev E Stat Nonlin Soft Matter Phys 71(3 Pt 1):031401
16. Matson W R, Ackerson B J, Tong P (2003) Pattern formation in a rotating suspension of non-Brownian settling particles. Phys Rev E Stat Nonlin Soft Matter Phys 67(5 Pt 1):050301
17. Matson W R, Ackerson B J, Tong P (2010) Patterns in a suspension contained in a horizontally rotating cylinder. Chaos 20:041102
18. Kalyankar M G, Matson W R, Tong P, and Bruce J. Ackerson B J (2008) Pattern formation in a rotating suspension of non-Brownian buoyant particles. Phys. Fluids 20:083301
19. PCR Application Manual 3rd Edition. Roche. https://www.roche-applied-science.com/publications/print_mat/pcr_application_manual_3rd_edition.pdf While the foregoing is directed to embodiments of the present invention, other and further embodiments of the invention may be devised without departing from the basic scope thereof, and the scope thereof is determined by the claims that follow. Any claim below that is written as dependent on an independent claim can also be written as dependent on any of the claims under such independent claim, except where logic forecloses such a dependency.

What is claimed is:

1. A light-triggered microtransponder reader for light-triggered microtransponders placed in a vessel comprising:
   a stochastic sampling device configured to receive the vessel;
   a source of light configured to enter the vessel and selectively illuminate the microtransponders and trigger their transmission of their ID; and
   a microtransponder ID radio receiver configured to collect ID data from the microtransponders as they are selectively illuminated and thereby triggered to send ID data, wherein the vessel is configured to hold 10 to 10,000 said microtransponders, and the stochastic sampling device is configured to rotate the vessel such that 80% of the microtransponders are triggered to determine the associated ID within 1000 seconds.

* * * * *